(12) United States Patent
Buechler et al.

(10) Patent No.: US 9,464,328 B2
(45) Date of Patent: Oct. 11, 2016

(54) BIOMARKERS AND USES THEREOF IN PROGNOSIS AND TREATMENT STRATEGIES FOR RIGHT-SIDE COLON CANCER DISEASE AND LEFT-SIDE COLON CANCER DISEASE

(71) Applicant: THE UNIVERSITY OF NOTRE DAME, Notre Dame, IN (US)

(72) Inventors: Steven Buechler, Granger, IN (US); Amanda B. Hummon, Granger, IN (US)

(73) Assignee: UNIVERSITY OF NOTRE DAME, Notre Dame, IN (US)

( * ) Notice: Subject to any disclaimer, the term of this patent is extended or adjusted under 35 U.S.C. 154(b) by 0 days.

(21) Appl. No.: 14/454,552

(22) Filed: Aug. 7, 2014

(65) Prior Publication Data
US 2015/0073035 A1    Mar. 12, 2015

Related U.S. Application Data

(62) Division of application No. 13/332,071, filed on Dec. 20, 2011, now abandoned.

(60) Provisional application No. 61/462,592, filed on Feb. 4, 2011, provisional application No. 61/459,864, filed on Dec. 20, 2010.

(51) Int. Cl.
C12Q 1/68         (2006.01)
G01N 33/574      (2006.01)

(52) U.S. Cl.
CPC ....... *C12Q 1/6886* (2013.01); *G01N 33/57419* (2013.01); *C12Q 2600/106* (2013.01); *C12Q 2600/118* (2013.01); *C12Q 2600/158* (2013.01); *G01N 2800/54* (2013.01)

(58) Field of Classification Search
None
See application file for complete search history.

(56) References Cited

U.S. PATENT DOCUMENTS

| 2003/0186302 A1 | 10/2003 | Wang |
| 2005/0014165 A1 | 1/2005 | Lee et al. |
| 2010/0136571 A1 | 6/2010 | Arpin et al. |

FOREIGN PATENT DOCUMENTS

| EP | 1 355 149 | 10/2003 | | |
| WO | 2005010486 | 2/2005 | | |
| WO | WO 2007027509 A2 | * 3/2007 | ............. | C07K 16/18 |
| WO | WO 2009143603 A1 | * 12/2009 | ........... | C12Q 1/6886 |
| WO | 2010132817 | 11/2010 | | |

OTHER PUBLICATIONS

EST Profile for Hs.371036—NOX4: NADPH oxidase 4, printed from http://www.ncbi.nlm.nih.gov/UniGene/ESTProfileViewer.cgi?uglist=Hs.371036 as pp. 1/3-3/3 on Sep. 10, 2015.*
EST Profile for Hs.375129—MMP3: Matrix metallopeptidase 3 (stromelysin 1, progelatinase, printed from http://www.ncbi.nlm. nih.gov/UniGene/ESTProfileViewer.cgi?uglist=Hs.375129 as pp. 1/3-3/3 on Sep. 10, 2015.*
EST Profile for Hs.174249—CDX2: Caudal type homeobox 2, printed from http://www.ncbi.nlm.nih.gov/UniGene/ESTProfileViewer.cgi?uglist=Hs.174249 as pp. 1/3-3/3 on Sep. 10, 2015.*
Affymetrix Technical Manual (701021 rev. 4) for GENECHIP® Expression Analysis (Affymetrix, Santa Clara, CA), © 1999-2003.*
Jorissen et al. Metastasis-associated gene expression changes predict poor outcomes in patients with Dukes Stage B and C colorectal cancer. Clinical Cancer Research, vol. 15, pp. 7642-7651, Dec. 8, 2009, including Supplementary Tables 1-3, printed as pp. 1/49-49/49.
GEO Series accession No. GSE14333, http://www.ncbi.nlm.nih.gov/geo/query/acc.cgi?acc=GSE14333, publicly available Jan. 8, 2010, printed as pp. 1/2-2/2.
GEO Sample accession No. GSM358408, http://www.ncbi.nlm.nih.gov/geo/query/acc.cgi?acc=GSM358408, publicly available Jan. 8, 2010, printed as pp. 1/2-2/2, including the full table printed as pp. 1/912-912/912.
GenBank Accession No. XM_542262, GI: 73987961, publicly available Aug. 2005, printed as pp. 1/2-2/2.
GenBank Accession No. NM_016931, GI: 219842344, publicly available Oct. 2009, printed as pp. 1/7-7/7.
GenBank Accession No. NM_001 002967.1, GI: 50950194, publicly available Sep. 2009, printed as pp. 1/2-2/2.
GenBank Accession No. NM_002422, GI: 73808272, publicly available Nov. 2009, printed as pp. 1/6-6/6.
Bauer, Kerry M., et al., "Comparative label-free LC-MS/MS analysis of colorectal adenocarcinoma and metastatic cells treated with 5-fluorouracil", Proteomics, 2012, pp. 1928-1937, WILEY-VCH Verlag GmbH & Co.
Bauer, Kerry M., et al., "Effects of the miR-143/-145 MicroRNA Cluster on the Colon Cancer Proteome and Transcriptome", Journal of Proteome, 11, 2012, pp. 4744-4754, American Chemical Society.
Hummon, Amanda, B., et al., "Systems-wide RNAi analysis of CASP8AP2/FLASH shows transcriptional deregulation of the replication-dependent histone genes and extensive effects on the transriptome of colorectal D cancer cells", Molecular Cancer, 2012 pp. 1-22, BioMed Central.

(Continued)

*Primary Examiner* — Jennifer Dunston
(74) *Attorney, Agent, or Firm* — Husch Blackwell LLP; Denise L. Mayfield

(57) ABSTRACT

Genetic biomarkers for left side colon cancer (LCC) (such as expression levels of an RNA transcript or expression product of NOX4, MMP3, or a combination) and right side colon cancer (RCC) (such as expression levels of an RNA transcript or expression product of CDCX2, FAM69A, or a combination), are disclosed. Methods for using the biomarkers in providing a prognosis of relapse-free survival probability in patients having LCC or RCC are also presented. Prognostic panels using gene expression values of the biomarkers are also presented. Computer implemented methods employing the biomarkers, and as well as for determining relapse-free survival probability in a patient having RCC or LCC are provided. A genetic method for classifying a colon cancer tissue as a RCC or as a LCC is also disclosed.

31 Claims, 6 Drawing Sheets

(56) References Cited

OTHER PUBLICATIONS

Xiao-Shan, Yue, et al., "Mass spectrometry-based phosphoproteomics in cancer research", Front. Biol., Sep. 4, 2012, pp. 566-586, vol. 7(6).

Park, H.S. et al, 'Impaired generation of reactive oxygen species in leprechaunism though downregulation of Nox4', Diabetes, Nov. 2005, pp. 3175-3181, vol. 54, No. 11.

Brenner, H. et al., 'Protection from right- and left-sided colorectal neoplasms after colonoscopy: Population-based study', J. Natl. Cancer Inst., Dec. 30, 2009, pp. 89-95, vol. 102.

Bauer, K. M. et al, 'Right-Side and Left-Side Colon Cancer Folow Different Pathways to Relapse', Molecular Carciogenesis, Jun. 7, 2011, pp. 411-421, vol. 51, No. 5.

International Search and Written Opinion, mailed on Aug. 22, 2012 in PCT/US2011/066233.

Extended European Search Report, completed on Dec. 12, 2014 in EP 11 85 0360.

* cited by examiner

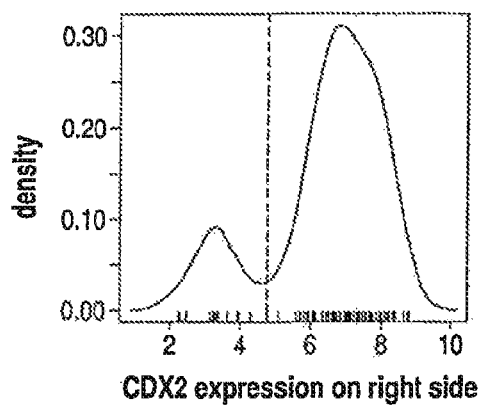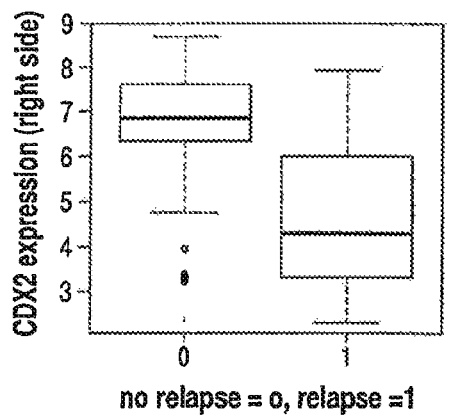
FIG. 2A  FIG. 2B
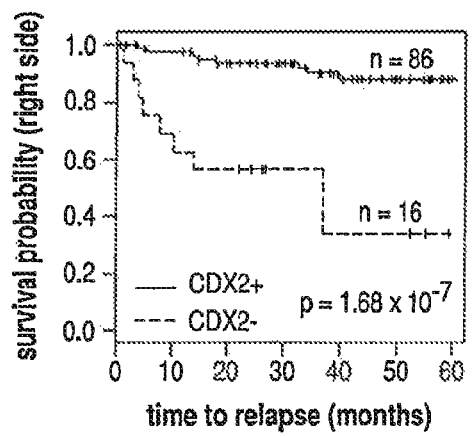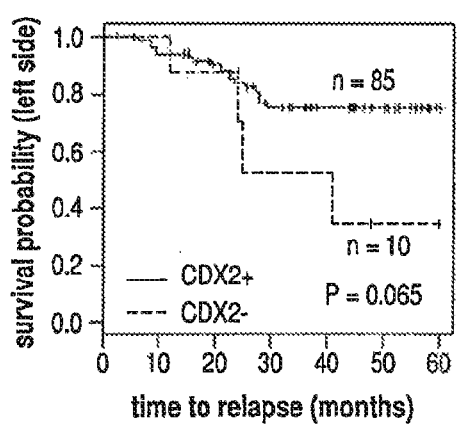
FIG. 2C  FIG. 2D

BIOMARKERS AND USES THEREOF IN PROGNOSIS AND TREATMENT STRATEGIES FOR RIGHT-SIDE COLON CANCER DISEASE AND LEFT-SIDE COLON CANCER DISEASE

CROSS-REFERENCE TO RELATED APPLICATIONS

The present application is a divisional of the U.S. patent application Ser. No. 13/332,071 filed Dec. 20, 2011 to which priority is claimed. U.S. Ser. No. 13/332,071 is a utility application which claims priority to U.S. Provisional Patent Application 61/459,864 filed Dec. 20, 2010 and also claims priority to U.S. Provisional Patent Application 61/462,592, filed Feb. 4, 2011. The entire content of U.S. Ser. No. 61/459,864 and U.S. Ser. No. 61/462,592, and U.S. Ser. No. 13/332,071 is specifically incorporated herein by reference.

SEQUENCE LISTING

The instant application contains a Sequence Listing which has been submitted electronically in ASCII format and is hereby incorporated by reference in its entirety. Said ASCII copy, created on Aug. 7, 2014, is named 520837-0000070_SL.txt and is 45,175 bytes in size.

BACKGROUND

Thousands of people around the world have been diagnosed with colon cancer, hundreds ultimately dying of the disease. Patients are typically treated with colon resection surgery, followed by radiation therapy or systemic chemotherapy, the therapy being based on macroscopic traits of the tumor and the tumor stage. The 5-year relapse-free survival rate is improved in some patients receiving chemotherapy after colon surgical resection surgery, while this statistic is not improved in others.

Diagnostic tests for predicting relapse in colon cancer include the Oncotype DX test (Genomic Health). However, Genomic Health's test and others reports of a test for relapse in colon cancer is widely considered a failure. The Oncotype DX Colon test identifies a small group of poor prognosis patients, but the test does not isolate good prognosis patients who can avoid further therapy, such as chemotherapy. Unfortunately, there does not exist a prognostic test for colon cancer that provides a consistent and accurate assessment of colon relapse risk in clinical practice.

Painful and expensive therapies, such as chemotherapy, are typically part of a standard and routinely proscribed clinical care management protocol for the post-colon cancer resection patient. Chemotherapy is routinely recommended for patients with stage III or IV tumors.[1] While chemotherapy is of some benefit for stage II colon cancers[1], 82% of these patients will survive for 5 years without further treatment.[1] Only about 10% of the patients who do not receive chemotherapy reportedly die of the disease within 5 years. A method of predicting the patient population that can safely avoid chemotherapy apart from that population that will likely benefit from chemotherapy, will save lives, relieve thousands of people from the toxic side effects of unnecessary chemotherapy, and save significant healthcare expense worldwide. However, there is no reliable method in existence that is capable of accurately predicting which of these patient populations could successfully avoid the painful and toxic process of chemotherapy without risk of relapse.

There is growing evidence that right-side colon cancer (RCC) and left-side colon cancer (LCC) have significantly different histological and molecular characteristics. For example, RCC is more common in women than men, and patients with RCC have a poorer prognosis than patients with LCC[3,4]. RCC and LCC tend to have different gross macroscopic pathology[5]. At the molecular level, a significant number of genes are differentially expressed between RCC and LCC[6], and patterns of loss of heterozygosity and promoter methylation vary by location[7].

Despite these observations, the challenge of colon cancer treatment remains to target specific treatment regimens to pathogenically distinct tumor types, and ultimately personalize colon cancer treatment in order to maximize outcomes. Hence, a need exists for materials and tests that are simultaneously prognostic and provide predictive information about colon cancer patient responses to treatment options. A medical need continues to exist for improved colon cancer clinical screening tools to enable more effective and less toxic colon cancer care and treatment management, and that also closely correlates with a high confidence level of long-term, relapse-free survival probability after colon cancer resection surgery.

SUMMARY OF THE INVENTION

In a general and overall sense, the present invention provides powerful and highly significant biomarkers for quantifying risk of recurrence of location-specific colon cancer. The present disclosure demonstrates that different processes dominate disease progression in left-side colon cancer (LCC) and right-side colon cancer (RCC), and that genes that are most predictive of relapse in LCC are much less significant in RCC, and vice-versa. Thus, using the information of the present disclosure, highly accurate and specific molecular tools are provided that can identify a patient as having LCC disease apart from those with RCC disease, and as a consequence of this, enable methods for highly accurate and effective techniques of prognosis assessment and treatment tailored to the disease type of the patient. In this way, methods for treating LCC and RCC as separate diseases are now possible.

The present disclosure identifies specific, previously unknown, colon cancer location specific biomarkers. The specific colon cancer biomarkers are demonstrated to have a bimodal distribution pattern of expression. Specific biomarkers for left side colon cancer (LCC) and for right side colon cancer (RCC) are provided. LCC and RCC disease may be identified in the patient for example, by measuring expression levels of PRAC gene or by the clinical identification of the colon location site from which the colon cancer/tumor tissue sample was harvested. Then, the RCC and LCC biomarkers disclosed herein may be used to provide a predicted prognosis of the patient, from which a specific LCC or RCC clinical treatment plan may be formulated.

The specific and different genetic biomarkers of the invention separates each disease group population of colon cancer patients, the LCC disease group and RCC disease group population, into a good prognosis group and a poor prognosis group. Specifically, the LCC disease group population is divided into a poor prognosis LCC population group and a good prognosis LCC population group. The RCC disease group population is divided into a poor prognosis RCC patient population group and a good prognosis RCC patient population group. The biomarkers possess a bimodal distribution among these specific populations of colon cancer patients, and may be used as part of the presently described methods to provide location specific left-side or right-side colon cancer tumor disease assessment. Use of the biomarkers provides an improved and more accurate quantifier of risk of colon cancer relapse and of survival probability compared to tumor stage alone.

The bimodal genetic biomarkers for left-side colon disease and right side colon disease include NOX4, MMP3, CDX2 and FAM69A. These biomarkers have particular individual and distinct genetic expression level profiles. Differences in the expression level profiles and their distribution within a colon cancer population, RCC or LCC, correlates with the status of a patient as having a good prognosis of survival or as a patient with a bad prognosis of survival.

Genes NOX4 and MMP3 have a specific bimodal expression profile in left side colon cancer disease colon tissue that identifies a patient as having either a good or bad prognosis for 5-year relapse free survival.

Genes CDX2 and FAM69A have a specific bimodal expression profile in right side colon disease colon tissues that identifies a patient as having either a good or bad prognosis for 5-year relapse free survival.

In specific embodiments, in a population of colon cancer patients having left side colon cancer (LCC) disease, a patient whose tumor expresses a high level of a specific gene or set of genes, such as gene NOX4, are at higher risk for colon cancer relapse within a 5 year post-surgical period. Such patients would be identified as in need of chemotherapy or other treatment to improve their chances of survival, whereas those expressing a low level of NOX4 are not at a higher risk for relapse, and therefore would not be in need of treatment such as chemotherapy or the like to improve their chances of a 5-year relapse free survival.

In another form of colon cancer disease, in a population of colon cancer patients having right side colon cancer (RCC) disease, a patient whose tumor or tumor tissue (the tumor tissue being obtained from the right side of the colon in the patient) has a low gene expression level of a set of RCC-elated genes comprising CDX2, FAM69A, or both, compared to a threshold expression value/level of a like-set of RCC related genes, is associated with poor prognosis and high expression levels with good prognosis. Here, low expression is relative to a threshold value/level of the like RCC-related genes, such as CDX2, in a population of RCC patients that have a known 5-year history of relapse and relapse-free survival. In a particular embodiment, a method is provided for prognosis of right-side colon cancer patients. As part of this method, colon cancer patients having right-side colon cancer disease with colon tissue expressing a low level of gene CDX2 compared to a threshold expression value/level for CDX2, are at higher risk for colon cancer relapse within a 5-year post-surgical period. This patient and/or patient population would be identified as in need of chemotherapy or other treatment to improve their chances of survival, whereas those expressing a high level of CDX2, are not at a higher risk for relapse, and therefore would not be in need of treatment such as chemotherapy or the like to improve their chances of a 5-year relapse free survival.

Relapse patients with RCC have been identified here to demonstrate accelerated cell cycle progression and elevated Wnt signaling. Axin 2 is also identified to be downregulated in RCC relapse patients.

In other aspects, improved methods for managing the clinical care of a patient having been diagnosed with colon cancer are provided. In particular, the present invention provides, in some aspects, a method for identifying the best clinical management for the treatment of a left-side colon cancer (LCC) patient, following surgical intervention to remove the cancer, as well as a method for identifying the best clinical management for the treatment of a right side colon cancer (RCC) patient following surgical removal of the cancer.

In some embodiments, the assessment of gene expression levels of a defined panel of genes may be measured using GeneChip®. or microarray technology. While any number of standard microarray platforms known to those of skill in the art may be used, an example of one commercially available microarray is the GeneChip®. (Affymetrix®.).

Right Side Colon Cancer (RCC)—Biomarkers, RCC Disease and Treatment:

Biomarker for Right-Side colon cancer—CDX2, FAM69A, CDKN2B, GADD45A and CCND 1. Other RCC indicative molecules associated with relevant RCC biological pathways include cyclic dependent kinase inhibitor 2B (CDKN2B), growth arrest and DNA damage inducible, alpha (GADD45A) and cyclin D1 (CCND1).

A significant percentage of RCC patients that experience a colon cancer relapse after surgical intervention have been determined, according to the methods of the present invention, to present right side colon cancer samples that demonstrate low expression levels of caudal type homeobox 2(CDX2). Here, low expression is relative to the DCX2 expression levels of the RCC cancer tumors in a population of all RCC cancer patients. Unlike other CDX2 tests, the present model provides a highly prognostic indicator concerning relative risk for recurrent colon cancer relapse. Prior description of the use of the CDX2 gene as a colon cancer has been mixed, with the CDX2 gene having been used only in identifying a patient as having a cancer of the right side of the colon or not.23 While some report CDX2 as increased in colon tumors, others report it decreased.

According to the present invention, a RCC patient with low CDX2 expression levels, accordingly, would likely be proscribed a more aggressive, post colon surgery, treatment regimen, such as chemotherapy and/or radiation therapy.

Conversely, a RCC patient with relatively high expression levels of CDX2 has a lower risk of recurrence than the overall population of patients diagnosed with RCC disease. The 5-year expected survival probability is sufficiently high that the patient would not benefit from systemic chemotherapy, radiation therapy, or other post-colon cancer resection surgery.

Patient samples from RCC patients having a high probability of colon cancer relapse, and a decreased probability of 5-year survival probability without relapse, also evidence down regulation of Axin 2, elevated levels of cyclic dependent kinase inhibition 2B (CDKN2B), elevated expression levels of growth arrest and DNA damage inducible, alpha (GADD45A), and elevated expression levels of cyclin D1 (CCND1).

Table 1 provides a chart of the biomarker genes, and the probes employed to assess the gene expression. These commercially available gene probe families are provided here for example only, as other genetic probes for the identified biomarker genes may be devised by one of skill in the at and employed in the practice of the present invention employing the teachings of the present disclosure.

TABLE 1

| PROBE | SYMBOL | NAME | ACCN | PROGNOSIS POOR | GOOD |
|---|---|---|---|---|---|
| 216044_x_at | FAM69A | family with sequence similarity 69, member A | AK027146 | LOW | HIGH |
| 206387_at | CDX2 | caudal type homeobox 2 | U51096 | LOW | HIGH |
| 225582_at | ITPRIP | inositol 1,4,5-trisphosphate receptor interacting protein; | AA425726 | HIGH | LOW |
| 201474_s_at | ITGA3 | integrin, alpha 3 (antigen CD49C, alpha 3 subunit of VLA-3 receptor) | NM 002204 | HIGH | LOW |
| 225667_s_at | FAM84A | family with sequence similarity 84, member A | A1601101 | LOW | HIGH |
| 227123_at | RAB3B | RAB3B, member RAS oncogene family | AU156710 | HIGH | LOW |
| 218284_at | SMAD3 | SMAD family member 3 | NM_015400 | HIGH | LOW |
| 205559_s_at | PCSK5 | proprotein convertase subtilisin/kexin type 5 | NM 006200 | HIGH | LOW |
| 219909_at | MMP28 | matrix metallopeptidase 28 | NM_024302 | HIGH | LOW |

The good prognosis component of CDX2 in the right-side samples in GSE14333 contains 84% of the samples. The good prognosis component defined by using both CDX2 and FAM69A contains 80% of the samples.

NOX4 is largely unexpressed in RCC. This means that a test that examines NOX4 in a patient having RCC disease will result in a false "good prognosis" assessment of the patient.

As used in the description of the present invention, RCC refers to a tumor tissue and/or cancerous tissue that is identified from tissue harvested from the right side of the colon. The right side of the colon will be understood in the description of the present invention as that part of the human colon that extends from the cecum or ascending colon and extends through the transverse colon, excluding the appendix.

Left Side Colon Cancer (LCC)—Biomarkers, Disease and Treatment:

Biomarker for Left-Side Colon Cancer—NOX4 and MMP3.

The NOX family of genes has been implicated in cancer development by reactive oxygen species (ROS) in several forms of cancer12, but NOX4 has not been previously implicated in colon cancer progression.

A higher percentage of LCC patients that experience a colon cancer relapse after surgical intervention have been determined, according to the methods of the present invention, to present left side colon cancer samples with a higher expression levels of NOX4. These patient samples also evidence elevated integrin-binding sialoprotein (IBSP), and lower expression levels of matrix metallopeptidase 3 (stromelysin 1, progelatinase) (MMP3).

Therefore, a higher NOX4 expression level in a left-side colon cancer tissue would be indicative of a higher risk of colon cancer relapse. Thus, this patient population would more likely benefit in a higher probability of increased survival without relapse and decreased risk of colon cancer metastasis if additional, post-colon surgery, treatments were administered, such as chemotherapy and/or radiation therapy.

A LCC patient with low NOX4 expression levels has a high probability of relapse-free survival for 5 years. Such a patient is unlikely to benefit from systemic chemotherapy, radiation therapy, or other post colon cancer resection surgery procedure.

In some embodiments, a panel of gene biomarkers for good prognosis LCC patients may be obtained by combining 2 or more genes in Table 2. A set of good prognosis patients is the intersection of the good prognosis components of the individual genes in the panel. Table 2 provides a chart of the biomarker genes, and the probe employed to assess the gene expression. These are exemplary, as other genetic probes for the identified biomarker genes may be devised by one of skill in the at and employed in the practice of the present invention employing the teachings of the present disclosure.

TABLE 2

| PROBE | SYMBOL | NAME | ACCN | PROGNOSIS POOR | GOOD |
|---|---|---|---|---|---|
| 205828_at | MMP3 | matrix metallopeptidase 3 (stromelysin 1, | NM_002422 | LOW | HIGH |
| 230748_at | SLC16A6 | solute carrier family 16, member 6 (monocarboxylic acid transporter 7) | A1873273 | HIGH | LOW |
| 205990_s_at | WNT5A | wingless-type MMTV integration site family, member 5A | NM_003392 | LOW | HIGH |
| 202435_s_at | CYP1B1 | cytochrome P450, family 1, subfamily B, polypeptide 1 | AU154504 | HIGH | LOW |
| 219773_at | NOX4 | NADPH oxidase 4 | NM 016931 | HIGH | LOW |
| 236028_at | IBSP | integrin-binding sialoprotein | BE466675 | HIGH | LOW |
| 205286_at | TFAP2C | transcription factor AP-2 gamma (activating enhancer binding protein 2 gamma) | U85658 | HIGH | LOW |

TABLE 2-continued

| | | | | PROGNOSIS | |
|---|---|---|---|---|---|
| PROBE | SYMBOL | NAME | ACCN | POOR | GOOD |
| 206091_at | MATN3 | matrilin 3 | NM_002381 | HIGH | LOW |
| 204672_s_at | ANKRD6 | ankyrin repeat domain 6 | NM 014942 | HIGH | LOW |

A panel of gene biomarkers for good prognosis LCC patients is obtained by combining 2 or more genes in Table 5. A set of good prognosis patients is the intersection of the good prognosis components of the individual genes in the panel.

Conversely, a LCC patient with high NOX4, would likely be proscribed an aggressive post colon surgery treatment regimen. It is anticipated that this population of patients would benefit from an increase in probability of relapse free survival, or decreased probability of colon cancer metastasis, with subsequent aggressive clinical treatment, such as chemotherapy and/or radiation therapy. The good prognosis component of NOX4 in the left-side samples in GSE14333 contains 56% of the samples. The good prognosis component defined by using both NOX4 and MMP3 contains 51% of the samples.

As used in the description of the present invention, LCC refers to a tumor tissue and/or cancerous tissue that is identified from tissue harvested from the left side of the colon. The left side of the colon will be understood in the description of the present invention as that part of the human colon that begins at the left splenic flexure, includes the descending colon and ends with the sigmoid, but does not include the rectum.

In LCC samples, elevated expression of NADPH oxidase 4 (NOX4) (as compared to a threshold expression value/level of the gene in a LCC population of patients that have at least a 5-year history of relapse or as relapse-free) is highly predictive of relapse in post-colon surgery patients. CDX2 has normal expression levels in most LCC relapse cases.

The present analysis of the pathways affected by these genes point to their central role in colon cancer progression, giving a high level of confidence in these results.

Gene Panel Probes and Micro-Array Methods for Colon Disease Screening:

The present invention also provides a panel of genetic probes for assessing 5 year survival probability without relapse in a patient population having a cancerous left-side colon (LCC) tumor. These genetic probes are described herein in Tables 2 and 4.

The present invention also provides a panel of genetic probes for assessing 5 year survival probability without relapse in a patient population having a cancerous right-side colon (RCC) tumor. These genetic probes are described herein at Tables 1 and 5.

There are numerous other genes that can replace the genes presented in the present model with little loss of significance, so this should be viewed as a family of equivalent tests. RT-PCR in human colon cancer cell lines are demonstrated to have expected expression levels of the genes described as part of the present genetic panels, given the specific characteristics of the source tumors. Thus, the studies conducted with these cells lines are predictive of the expected gene expression characteristics of colon cancer in vivo.

Methods of the invention can be utilized in a number of different applications. For example, diagnostic chips can be fabricated based on the identification of the diagnostic genes, such as the ones identified herein at Tables 4 and 5. Such chips would be useful in clinical settings, as it would allow clinicians to diagnose a particular type of colon cancer from a relatively small set of genes, instead of purchasing entire gene sets.

The methods of the present invention may take the form of a diagnostic and/or screening tool that is provided in the form of an array of genetic probes specific for the colon cancer biomarkers described herein.

The term "array" as used in the present invention refers to a grouping or an arrangement, without being necessarily a regular arrangement. An array comprises preferably at least 2, more preferably 5 different sets of detection molecules or patient samples. Preferably, the array of the present invention comprises at least 50 sets of detection molecules or patient samples, further preferred at least 100 sets of detection molecules or patient samples. The detection molecule can be for example a nucleic acid probe, such as the nucleic acid probes provided at Table 4 (for LCC disease), Table 5 (for RCC disease), or in some embodiments, the nucleic acid probes of both Tables 4 and 5. The described array can be used in a test system according to the invention. The array can be either a micro array or a macro array.

The detection molecules are immobilized to a solid surface or support or solid support surface. This array or microarray is then screened by hybridizing nucleic acid probes prepared from patient samples or by contacting the array with proteinaceous probes prepared from patient samples.

The support can be a polymeric material such as nylon or plastic or an inorganic material such as silicon, for example a silicon wafer, or ceramic. Pursuant to a preferred embodiment, glass (Si02) is used as solid support material. The glass can be a glass slide or glass chip. Pursuant to another embodiment of the invention the glass substrate has an atomically flat surface.

Methods of the invention can also be used for identifying pharmaceutical targets. Pharmaceutical companies can utilize methods of the invention to determine which genes to target in efforts to target specific right-side colon disease or left-side colon disease.

The method may further include the step of producing a report indicating a RCC or LCC prognosis for the colon cancer patient based on the expression levels and a comparison to other patients with similar expression levels, and optionally, calculating a recurrence score based on the expression levels.

Computerized Methods:

According to an embodiment of the invention, any of the steps of the methods may be performed by a computer. In one embodiment, the expression level of the gene panel is performed by microarray analysis with multi-state probes specific to the genes of the gene panel.

In one embodiment, a computer running a software program analyzes gene expression level data from a patient, compares that data to a distribution of expression levels from a population of colon patients having a RCC or LCC disease state, and determines whether the patient's expression levels have a +/− status for each gene identified herein as informative to an RCC or LCC prognosis, respectively.

As described herein, the +/− status of a LCC or RCC patient's colon tumor tissue gene expression is determined based on comparing that patient's colon sample tissue level of gene expression to the density distribution of gene expression from all LCC or RCC patients in a sample group. In one embodiment, density distribution of expression levels from the sample population is determined based on mixture model fit statistical method which is a statistical method known to those of skill in the art. A key discovery according to one aspect of the invention as described herein is that the expression by LCC or RCC cancer patients of multi-state genes, as described herein, presents at least a bimodal distribution when the expression level density distribution is determined using the mixture model fit method. Because of this at least bimodal distribution, it is possible to determine a threshold whereby on one side of the threshold, the level of gene expression is low and on the other side of the threshold, the level of gene expression is high. Correlation of a high expression level or low expression level to a good or bad prognosis depends on the type of colon cancer disease as LCC or RCC, as well as the specific bimodal gene expression level being examined, as is more fully described herein.

Based on the expression level status for each gene, the computer software is capable of determining the prognosis for the patient as being good or poor. For example, the software is capable of generating a report summarizing the patient's gene expression levels and/or the patient's (+) or (−) status scores, and/or a prediction of the likelihood of long term survival of the patient and/or the likelihood of recurrence or metastasis of the patient's LCC or RCC disease condition. Further, in one embodiment, the computer program is capable of performing any statistical analysis of the patient's data or a population of patient's data as described herein in order to generate the + or − status of the patient.

Further, in one embodiment, the computer program is also capable of normalizing the patient's gene expression levels in view of a standard or control prior to comparison of the patient's gene expression levels to those of the patient population. In some embodiments, the computer is capable of ascertaining raw data of a patient's expression values from, for example, immunohistochemical staining or a microarray, or, in another embodiment, the raw data is input into the computer.

Reactive Oxidative Species (ROS) Production in Colon Cancer:

Methods for inhibiting reactive oxidative species production in colon cancer cells are provided, wherein carcinogenic colon cancer shall be inhibited. Overproduction of reactive oxidative species (ROS) have long been implicated in the aggressiveness of cancer tumors. Interference RNA for NOX4 may be used to inhibit the aggressiveness of LCC tumors by reducing ROS production. ROS production in a colon cancer cell line, SW620, was reduced by inhibiting NOX4 mRNA using interference RNA. ROS production in LCC may also be inhibited by interfering with the activity of the NOX4 protein using an antibody.

The methods of the present invention are carried out with colon sample material such as a colon tumor tissue sample which already has been isolated from the human body. Subsequently the sample material can be fractionated and/or purified. It is for example possible, to store the sample material to be tested in a freezer and to carry out the methods of the present invention at an appropriate point in time after thawing the respective sample material.

After transformation of colorectal adenoma into colorectal cancer, the pathological condition of the afflicted individual can be further exacerbated by formation of metastasis. The present invention may be used to discriminate and identify early colon cancer, thus permitting the detection of the colon cancer disease at an early and still benign stage, an early stage or benign stage and/or early colon tumor stages. The early detection enables the physician to timely remove the colorectal adenoma and to dramatically increase the chance of the individual to survive.

According to the invention, the expression levels from the population of right side colon cancer (RCC) disease patients or left side colon cancer (LCC) disease patients for each gene in the colon cancer gene panel comprises a bimodal density distribution such that a statistically significant threshold exists between the two modes, whereby expression levels on one side of the threshold are deemed high and expression levels on the other side of the threshold are deemed low. The LCC or RCC patient sample is classified as demonstrating a relatively low expression level or a relatively high expression level of the informative gene or set of genes for LCC or RCC as defined here (See Tables 1 and 2), and the expression level is compared to a threshold expression value/level of a like gene or set of like genes. The prognosis in the RCC or LCC patient is then assessed based upon the specific gene expression data obtained from an existing pool of genetic expression profile data collected from the RCC or LCC disease patients, respectively, having a known positive 5 year colon cancer free survival history and a specific LCC or RCC genetic profile expression level data set. By way of example, this data set is a data set of mRNA expression values for NOX4 and MMP3 (for LCC), and CDX2 and FAM69A (for RCC).

The expression level profiles and diagnostic methods of the present RCC and LCC disease models provided here employing the bimodal genes identified for RCC and LCC are completely independent of and unrelated to the estrogen receptor (+) or (−) status of the tissue sample and any bimodal gene identified for breast cancer, and is unrelated to assessment of breast cancer prognosis or risk of relapse for breast cancer.

According to a further embodiment, the density distribution is determined by mixture model fit statistical analysis. According to one embodiment, the expression levels of each RCC or LCC gene from the respective population of RCC or LCC patients forms a density distribution of at least two or more modes and a statistically significant threshold exists between the two or more modes. Expression levels on one side of a defined threshold are deemed positively correlated with mortality and expression levels on the other side of a defined threshold are positively correlated with survival. According to a further embodiment, the density distribution is determined by mixture model fit statistical analysis.

A data set of mRNA expression values may be generated using, for example, an AFFYMETRIX microarray. One array may be generated for each patient in the cohort. Consider an array probe p such that increased expression is statistically significant in a univariate Cox proportional hazard model of relapse.

For purposes of the present methods, "p" is designated multi-state in this cohort if the density distribution can be partitioned into two components: a large normal component of expression values below a threshold c, and a long right tail with expression values above c. The component of high expression values, denoted "p+", contains a greater percentage of patients who relapse than the component of low expression values, denoted "p−".

BRIEF DESCRIPTION OF THE FIGURES

FIG. 2A. Low CDX2 expression is a significant predictor of relapse in right-side colon cancer. The density distribution of CDX2 expression in the right-side tumors on GSE14333 with Dukes Stage A, B or C follows a bimodal distribution. The multistate methodology divides the samples at an expression value of 4.76; the samples with expression below 4.76 are in the CDX2− component, and those with expression values above 4.76 are in CDX2+. FIG. 2B. The boxplot of CDX2 expression versus the relapse event vector illustrates the significance of the dependence. In this case, low CDX2 expression is predictive of relapse. FIG. 2C. The Kaplan-Meier curves for the CDX2+ and CDX2− components plot the expected survival probabilities for the components in the right-side tumors. The 5-year expected survival probability for CDX2+ is 0.88 95% CI (0.80-0.96) and for CDX2− it is 0.39 95% CI (0.15-0.78). A Cox proportional hazard model whose only variable is an indicator for the CDX2 components has a logrank test p-value 1.68×1 CDX2+ contains 86 samples and CDX2− contains 16 samples. FIG. 2D. The corresponding Kaplan-Meier plots for the CDX2 components in the left-side tumors shows a distinctly lower connection with relapse than on the right side. The 5-year expected survival for CDX2+ on the left side is 0.75 95C1% (0.66-0.86) and for CDX2− it is 0.35 95% CI (0.12-1.0). On the left side 10 samples are in CDX2− and 85 are in CDX2+.

DETAILED DESCRIPTION OF THE PREFERRED EMBODIMENTS

Figure 1A:
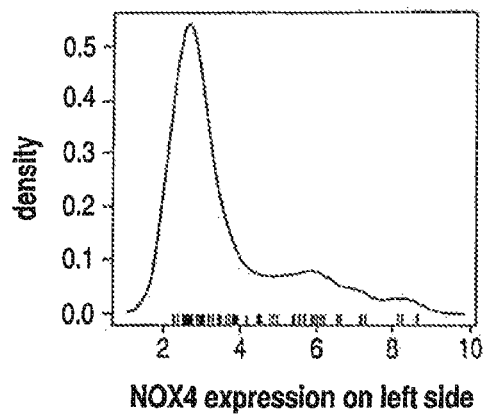
FIG. 1A. Elevated NOX4 expression is a significant predictor of relapse in left-side colon cancer. The density distribution of NOX4 expression in the left-side tumors on GSE14333 with Dukes Stage A, B or C shows a large component with low baseline expression and a tail of elevated expression values. Individual expression values are indicated with hatch marks at the lower edge. The multistate methodology divides the samples at an expression value of 3.1; the samples with expression below 3.1 are in the NOX4− component, and those with expression values above 3.1 are in NOX4+.

The present invention, in a general and overall sense, provides for biomarkers specific for left side colon cancer (LCC) and for right side colon cancer (RCC), as well as the use of these markers in providing powerful diagnostic and prognostic tools for predicting survival probabilities of patients with each disease.

In some embodiments, the invention provides for a method of measuring expression levels of the biomarker NOX4, MMP3, or a combination of these as an assessment indicator of left-side colon cancer (LCC) prognosis.

In another embodiment, the invention provides for a method of measuring expression levels of the biomarker CDX2, FAM69A, or a combination of these, as an assessment indicator of right-side colon cancer (RCC) prognosis.

In some embodiments, and to better facilitate use in conjunction with current practices in surgery and pathology, a clinically applicable version of the present methods may use RT-PCR to measure mRNA obtained from formalin-fixed, paraffin-embedded (FFPE) colon tissue.

The present invention demonstrates that different processes dominate progression to relapse in LCC and RCC. Using a microarray database and a method of building survival models, it is demonstrated here that genes that are most predictive of relapse in LCC are much less significant in RCC, and vice-versa. In particular, in the LCC samples, elevated expression of NADPH oxidase 4 (NOX4) is highly predictive of relapse, while NOX4 is largely unexpressed in RCC. The NOX family of genes has been implicated in cancer development by reactive oxidative species (ROS) in several forms of cancer14, but NOX4 has not been previously implicated in colon cancer progression. A significant percentage of the RCC samples that relapse have low expression levels of caudal type homeobox 2 (CDX2), while CDX2 has normal expression levels in most LCC relapse cases. Thus, it is shown that the LCC and RCC diseases possess non-overlapping diagnostic indicators that are specific for the disease, permitting more targeted treatment of the colon cancer patient.

The role of NOX4 in colon cancer is further investigated using the SW620 lymph-node metastasis colon adenocarcinoma cell line and RNA interference. NOX4 is expressed in the SW620 cell line, and application of NOX4 siRNA causes a significant reduction in ROS production.

Definitions: One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "sample material" is also designated as "sample".

The term "biomarker" is meant to designate a protein or protein fragment or a nucleic acid which is indicative for the incidence of the colorectal adenoma and/or colorectal carcinoma. That means the "biomarker" is used as a mean for detecting colorectal adenoma and/or colorectal carcinoma.

Unless defined otherwise, technical and scientific terms used herein have the same meaning as commonly understood by one of ordinary skill in the art to which this invention belongs. Singleton, et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

As used in the description of the present invention, "p" is defined as a microarray probe for a defined gene expression product. As used in the description of the present invention, a "multi-state gene" is defined as a gene capable of differential levels of expression within a LCC or RCC disease patient population such that the expression levels of the gene in the LCC or RCC disease patient population permits the patient population to be divided into at least two or more distribution groups based on density distribution according to statistical analysis of the expression level of specific LCC-associated (such as NOX4 and MMP3) or RCC associated (such as CDX2 and FAM69A) informative genes. For example, in one embodiment, the expression levels are divided into two groups based on a mixture model fit of expression levels of the gene of interest. In one embodiment, if the density distribution of gene expression for a particular gene of interest can be partitioned into at least two components, a large normal component of expression values below a threshold c, and a long right tail with expression values above c, the gene is a multi-state gene. Alternatively, in another embodiment, a gene is multi-state if the density distribution of gene expression for a particular gene of interest is partitioned into at least two components, a large normal component of expression values above a threshold c, and a long left tail with expression values below c.

Mixture Models. Given a numeric vector, the statistical method of finite mixture models partitions the vector into components, each of which is modeled by a different density distribution. The mixture models used to develop the methods described herein fit a pair of gaussian distributions to a vector. Such a model is described by a partition of the vector into components C1, C2, and a pair of gaussian distributions g1, g2 modeling the distributions of C1, C2, respectively.

The modeling process simultaneously partitions the vector and selects the means, .mu.1, .mu.2 and standard deviations .sigma.1, .sigma.2 of the two gaussian distributions, with the goal of giving the best possible fit over all alternatives. The fitting algorithm actually produces, for each point and component, a posterior probability that the point is in that component. The point is assigned to the component whose associated posterior probability is maximal. For a point p that is well-classified in, say, component 1, the posterior probability that p is in C2 will be very small. For convenience, posterior probabilities below a threshold Δ are reported as O. Following Leisch 2004, we use Δ=10-4. Points that are on the boundary between the two components will have posterior probability >Δ for both components. The "isolatedness" of, e.g., component 1 is assessed by the ratio, r1=n1/m1, where n1 is the size of C 1 and m1 is the number of elements with posterior probability of belonging to C 1 greater than A. Ratios are itoreq.1, with numbers close to 1 representing well-isolated components. Ratios are used to measure the ability of a mixture model fit to describe distinct states.

In most instances, the components defined by a fit of a pair of gaussian distributions consist of a pair of unbroken intervals. That is, there is a cutoff c so that one component consists of the values <c and the other component the values greater than or equal to c. In this way, mixture models can be used to calculate a threshold for dividing a vector into high and low components.

A standard measure of the quality of a mixture model fit is the likelihood, which is the product, over all points, of the maximal posterior probabilities. The likelihood can be used to decide, for example, if a fit with a pair of gaussian distributions is better than a fit with a single gaussian, or if a fit with Gamma distributions is better than a fit with gaussian distributions. Even better measures are AIC and BIC which adjust likelihood by the degrees of freedom. These measures play a part in defining the notion of a multi-state probe. According to one embodiment of this invention, mixture models were fit using the flexmix R package (Leisch, 2004).

"Probe" means a polynucleotide molecule capable of hybridizing to a target polynucleotide molecule. For example, the probe could be DNA, cDNA, RNA, or mRNA. In one embodiment, a probe is fixed, for example, by a covalent bond, to a solid state apparatus such as a microarray. The probe and the target may hybridize, for example, under stringent, or moderately stringent conditions. A probe may be labeled, for example, with a fluorescent or radiolabel to permit identification. In one embodiment, a probe is of a sufficient number of base pairs such that it has the requisite identity to bind uniquely with the target and not with other polynucleotide sequences such that the binding between the target and the probe provides a statistically significant level of accurate identification of the target molecule. In one embodiment, a probe's ability to bind a target is correlated to a statically significant prognostic indicator of a defined disease state as determinable using an identified panel of genes of interest. In one embodiment, the target is mRNA and the probe is a complementary piece of DNA or cDNA. In another embodiment, the target is cDNA or DNA and the probe is a complementary piece of mRNA. In another embodiment, the target is cDNA or DNA and the probe is a complementary piece of DNA.

The term "multi-state probe" is meant, in one embodiment, as a probe capable of hybridizing with a target polynucleotide molecule encoding a LCC or RCC specific multi-state gene. In another embodiment, a "multi-state LCC or RCC probe" means a probe capable of hybridizing with a target polynucleotide molecule encoding a relevant portion or fragment of a LCC or RRC multi-state gene, respectively. For example, the target polynucleotide molecule may be mRNA.

In one embodiment, a LCC or RCC multi-state probe (see Tables 1, 2, 4 or 5, respectively) is fixed to a solid state apparatus such as a microarray by, for example, a covalent bond. In one embodiment, hybridization between the probe and the target occurs under stringent conditions.

The term "hybridize" or "hybridizing" or "hybridization" refers to the formation of double stranded nucleic acid molecule between complementary sequences by way of Watson-Crick base-pairing. Hybridization can occur at various levels of stringency according to the invention. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel, et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Fico11/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 p.g/ml), 0.1% SDS, and 10% dextran sulfate at 42° C., with washes at 42° C. in 0.2.×SSC (sodium chloride/sodium citrate) and 50% formamide at 55° C., followed by a high-stringency wash consisting of 0.1×.SSC containing EDTA at 55° C. "Moderately stringent conditions" may be identified as described by Sambrook, et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×.SSC at about 37-50° C. The skilled artisan will recognize how to adjust the temperature, ionic strength, etc., as necessary to accommodate factors such as probe length and the like.

The term "microarray" refers to an ordered arrangement of hybridizable array elements, preferably polynucleotide probes, on a substrate.

The terms "differentially expressed gene," "differential gene expression," and their synonyms, which are used interchangeably, refer to a gene whose expression is activated to a higher or lower level in a subject suffering from a LCC or RCC disease, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or between various stages of disease development in a diseased subject.

The term "over-expression" with regard to an RNA transcript is used to refer to the level of the transcript determined by normalization to the level of reference mRNAs, which might be all measured transcripts in the specimen or a particular reference set of mRNAs.

The term "prognosis" is used herein to refer to the prediction of the likelihood of LCC or RCC cancer-attributable death or progression, including recurrence, metastatic spread, and drug resistance, of a neoplastic disease, such as RCC or LCC disease.

The term "prediction" is used herein to refer to the likelihood that a patient will respond either favorably or unfavorably to a drug or set of drugs, and also the extent of those responses, or that a patient will survive, following surgical removal or the primary LCC or RCC tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 3 years according to one embodiment, at least 8 years according to a more preferred embodiment, and at least 10 years according to a most preferred embodiment, following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "at least one," "at least two," "at least five," etc., of the genes listed in any particular gene set means any one or any and all combinations of the genes listed.

The term "node negative" cancer, such as "node negative" colon cancer, is used herein to refer to cancer that has not spread to the lymph nodes.

The term "gcrma" refers to a method know to those of skill in the art whereby raw data obtained from an Affymetrix.® microarray is normalized.

"Normalization" refers to statistical normalization. For example, according to one embodiment, a normalization algorithm is the process that translates the raw data for a set of microarrays into measure of concentration in each sample. A survey of methods for normalization is found in Gentleman, et al. For example, a microarray chip assesses the amount of mRNA in a sample for each of tens of thousands of genes. The total amount of mRNA depends both on how large the sample is and how aggressively the gene is being expressed. To compare the relative aggressiveness of a gene across multiple samples requires establishing a common baseline across the samples. Normalization allows one, for example, to measure concentrations of mRNA rather than merely raw amounts of mRNA.

"Biologically homogeneous" refers to the distribution of an identifiable protein, nucleic acid, gene or genes, the expression product(s) of those genes, or any other biologically informative molecule such as a nucleic acid (DNA, RNA, mRNA, iRNA, cDNA, etc.), protein, metabolic byproduct, enzyme, mineral, etc., of interest that provides a statically significant identifiable population or populations that maybe correlated with an identifiable disease state of interest.

"Low expression," or "low expression level(s)," "relatively low expression," or "lower expression level(s)" and synonyms thereof, according to one embodiment of the invention, refers to expression levels, that based on a mixture model fit of density distribution of expression levels for a particular multi-state gene of interest falls below a threshold c, whereas "high expression," "relatively high," "high expression level(s)" or "higher expression level(s)" refers to expression levels failing above a threshold c in the density distribution. The threshold c is the value that separates the two components or modes of the mixture model fit.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2nd edition (Sambrook, et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 4th edition); "Current Protocols in Molecular Biology" (F. M. Ausubel, et al., eds., 1987); and "PCR: The Polymerase Chain Reaction", (Mullis, et al., eds., 1994). The term "individual" or "individuals" is meant to designate a mammal. Preferably, the mammal is a human being such as a patient.

The term "healthy individual" or "healthy individuals" is meant to designate individual(s) not diseased of colorectal adenoma and/or colorectal carcinoma. That is to say, the term "healthy individual(s)" is used only in respect of the pathological condition of colorectal adenoma and/or colorectal carcinoma and does not exclude the individual to suffer from diseases other than colorectal adenoma and/or colorectal carcinoma.

The term "derivative thereof" is meant to describe any modification on DNA, mRNA or protein level comprising, e.g., the truncated gene, fragments of said gene, a mutated gene, or modified gene. The term "gene" includes nucleic acid sequences, such as DNA, RNA, mRNA or protein sequences or oligopeptide sequences or peptide sequences. The derivative can be a modification which is an result of a deletion, substitution or insertion of the gene. The gene modification can be a result of the naturally occurring gene variability. The term "naturally occurring gene variability" means modifications which are not a result of genetic engineering. The gene modification can be a result of the processing of the gene or gene product within the body and/or a degradation product. The modification on protein level can be due to enzymatic or chemical modification within the body. For example the modification can be a glycosylation or phosphorylation or farnesylation. Preferably, the derivative codes for or comprises at least 5 amino acids, more preferably 10 amino acids, most preferably 20 amino acids of the unmodified protein. In one embodiment the derivative codes for at least one epitope of the respective protein.

The term "patient" as used in the present application covers humans as well as non-human beings such as animals. The animals are preferably selected from the group consisting of rodents, e.g., mouse, rat, hamster, and other animals, e.g., guinea-pig, rabbit, hare, dog and pig.

These animals can be used to specifically induce certain disease states, like colorectal adenoma and colorectal carcinoma, for research purposes. The induction of said disease states can, for example, be effected by treatment of the animals, for example, with radioactive or chemical substances known to induce colorectal cancer or colorectal adenoma disease state. The disease states can also be induced using viral transfection systems. It is also possible to use genetically modified animals, in which one or more specific gene function(s) has/have been altered, or knock-out animals such as knock-out mice in which a specific gene function has been deleted.

The term "compound" can be one or more chemical substances, an antibody, protein, peptide, antisense mRNA, small molecular drug, or combinations thereof. The compound can also be replaced by irradiation, e.g., X-ray, or combinations of compounds and radiation can be used.

A good prognosis may be defined as a prognosis in which a patient is determined to be unlikely to benefit from cancer treatment such as chemotherapy or radiation, for example, subsequent to a colon cancer surgical procedure. This may be the case where the expression level of the identified bimodal gene or combination of genes for LCC or RCC disease is negatively correlated with mortality.

A poor prognosis patient is used to define a patient that is likely to benefit from further cancer treatment such as chemotherapy or radiation, for example, subsequent to a colon cancer surgical procedure. This may be the case where the expression level of the identified bimodal gene or combination of genes for LCC or RCC disease is positively correlated with mortality.

EXAMPLE 1

Identification of RT-PCR Primer-Probes that Measure in FFPE Tissue the mRNA Species Targeted by the ap-Colon Microarray Probes mRNA will be extracted from a number of colon cancer cell lines as well as from paraffin (FFPE) blocks prepared from these cell lines. This will enable direct assessment of the probes in the FFPE material and comparison with the "fresh state". Initial assessment will be performed using 13 different assay primer-probes pairs (8 from ap-Colon (two per gene) and 5 normalization controls). All assays will be performed in triplicate. The probes will be verified as providing comparable results in fresh tissues (cell lines) and matched FFPE counterparts. Quantitative RT-PCR with AACT methods for data analysis will be used to assess the utility of the probes. If suitable primer-probes cannot be found for the initial choice of genes, the list will be screened to identify replacement genes found in the development of ap-Colon. The RL-COLON pair of tests will use the primer-probes identified here.

Obtain archival FFPE colon cancer samples with data on disease stage and 5-year survival outcome. 50-100 samples from the right colon and the left colon will be obtained.

Use RL-COLON to verify differential expression of each gene in the panel in archival colon cancer tissue with varying stages. The tissue obtained will be divided in training and validation sets. The training set will be used to find thresholds between high and low expression levels of the genes in RL-COLON, replacing the thresholds in the microarray-based ap-Colon. The validation set is used to verify that RL-COLON is sufficiently predictive and prognostic to guide treatment decisions.

The pathway to relapse, metastasis and eventual death followed in a particular form of cancer is of fundamental concern in both cancer biology and treatment. Methods of stratifying breast cancer patients according to relapse risk have been developed using multi-gene measures of mRNA concentrations[9,10]. These tests measure the expression levels of numerous genes in the primary tumor and partition tumors into a poor prognosis group that is likely to metastasize, and a good prognosis group that is largely relapse-free. This work was framed around the clinical problem of identifying those patients who can avoid adjuvant chemotherapy with no significant increased risk of metastasis.

Several authors have proposed prognostic signatures for colon cancer However, none of these tests has the prognostic power seen in the breast cancer tests, and they are of questionable clinical value. While not intending to be bound by any particular theory or mechanism of action, the failure to find an effective panel of genes may be due, at least in part, to the existence of multiple disease subtypes that follow different pathways to progression.

EXAMPLE 2

Materials and Methods

The present example is provided to present the various materials, methods and statistical tools employed in the development and practice of the present invention.

Statistical analysis. The language R www.r-prqject.org/ was used for all statistical analyses. Survival models were fit with the R package survival. The microarray annotation package hgu133plus2.db in BioConductor www.bioconductor.org/ was also used. The proportional hazard condition was verified with the cox. zph function. All p-values in survival models refer to the p-value of the logrank score of a Cox proportional hazard model (CPH). A CPU is considered statistically significant if the p-value of the logrank score is <0.05.

Microarray dataset of colon cancer samples. In the present examples, the Gene Expression Omnibus (wvvw.ncbi.nirn.nih.gov/gds) data series GSE14333 was used. The characteristics of the data series GSE14333 are provided in Table 3.

Sample Preparation: The samples examined were colorectal cancer specimens from the H. Lee Moffit Cancer Center in the United States and Royal Melbourne Hospital, Western Hospital, and Peter MacCallum Cancer Center in Australia. Surgically isolated colorectal cancers were immediately frozen in liquid nitrogen. Total RNA was extracted from cancer tissue using TRIZOL (a mono-phasic solution of phenol and guanidine isothiocynate) reagent (Invitrogen). Approximately 8 micrograms of total RNA was processed to produce biotinylated cRNA targets.

After preparation, the samples were hybridized to Affymetrix GeneChip® hgu133plus 2 arrays. Expression values are computed from the CEL files with gcrma13. The survival endpoint reported in GSE14333 is any relapse, distant or local. Since the third quartile of time to relapse in the dataset is 28 months, the relapse data was censored to 60 months in the present examples. No further follow-up was available on the Dukes stage D samples. The characteristics of the tumors in the dataset are summarized in Table 3. More complete information about the patients is found in Jorisson, et al., (2008)13.

KEGG pathway analysis. The Kyoto Encyclopedia of Genes and Genomes (KEGG) www.genome.ip/k.egg/kegg2.html identifies the component genes in selected pathways. The BioConductor package hgu133plus2.db is used to associate array probes with pathways.

Multistate survival models. In Buechler, et al.[2], a method of defining survival models based on gene expression data is presented. In this system, an array probe (gene) is called multistate if the probe's expression values naturally divide samples into two distinct subtypes, much like the bimodality of the ESR1 gene divides samples into ER+ and ER− subgroups. For a multistate probe p there is a threshold c such that the samples with expression values above c, denoted p+, form one component, and the samples with expression values below c, denoted p−, form the second component. In the multistate probes that arise in survival models in cancer, one of the components is approximately normally distributed with a narrow variance, and the other smaller component is a tail to the right or left. Many genes have nearly normal expression distributions, hence are not considered multistate. The precise definition of a multistate probe is given in Buechler, et al.[2]

Colorectal cancer often develops through a specific genetic progression[17]. In the multistate genes that model the progression of cancer, one of the components is highly enriched in poor prognosis patients. To further exploit the principle that a multistate probe represents distinct states, the expression vector for a multistate probe is replaced by a binary variable which is 0 in the component of good prognosis samples and 1 in the poor prognosis component. Here, the significance of a multistate probe in a survival model is measured by the p-value of a logrank score of a Cox proportional Hazard Model (abbreviated CPH) using only the probe's binary variable.

Cell Culture. Colorectal cancer cell lines HCT-116, HT29, SW480, SW620 and SW837 were purchased from the American Type Culture Collection (ATCC; Manassas, Va.) and were maintained in RPMI 1640 medium (Invitrogen, Gaithersburg, Md.) containing 10% fetal bovine serum (Thermo Scientific, Pittsburgh, Pa.) and 2 mM L-glutamine (Invitrogen, Gaithersburg, Md.) and grown in 5% $CO^2$ at 37° C.

NOX4 silencing by siRNA. At 50-60% confluence, SW620 cells were transfected with one of two siRNA oligonucleotides targeting the NOX4 transcript. The sequences are referred to in the text as siRNA NOX4_5 and siRNA NOX4_8 and correspond with the following sequences:

```
5'-CCAGGAGAUUGUUGGAUAATT-3'-siRNA NOX4_5;
and

5'-GAGUUUCCAUAGGGAACUATT-3'-siRNA NOX4_8,

5'-CCAGGAGAUUGUUGGAUAATT-3' (SEQ ID NO: 1)-siRNA
NOX4_5;
and

5'-GAGUUUCCAUAGGGAACUATT-3' (SEQ ID NO: 2)-siRNA
NOX4_8,
```

Gene expression analysis. Total RNA was extracted from SW620 cells transfected with siRNA NOX4_5, siRNA NOX4_8 and control siRNA 48 hr post-transfection using RNEASY Mini kit (Qiagen, Germantown, Md.), following the animal cell protocol and homogenizing via 20 gage needles. Normal human colon RNA isolated postmortem from a donor was purchased from Ambion (Applied Biosystems, Foster City, Calif.). Nucleic acid quantity, quality and purity were determined using a Nanodrop 2000 UV-VIS spectrophotometer (Nanodrop, Rockland, Del.). cDNA was generated using the High-Capacity Reverse Transcriptase cDNA kit (Applied Biosystems, Foster City, Calif.) and 1.0 µg of total RNA according to the manufacturer's instructions. Quantitative PCR reactions were performed using the following primer sequences (Operon, Huntsville, Ala.): hypoxanthine phosphoribosyltransferase 1 (HPRT1),
HPRT1 For
5'-GC CATGAAGCAG GACTCTAAAGA-3' and
HPRT1 Rev
5'-TTGGCATAACACAGCTGATTGAT-3';
NOX4 For
5'-ATGTCAGTTGCTGCATTCCTAA-3' and
NOX4 Rev
5'-TCACTCAATAGTGCTGTGGTTT-3'.

Quantitative PCR was performed with a real-time PCR system, STEPONEPLUS (Applied Biosystems, Foster City, Calif.). Reactions were conducted with 300 ng of cDNA, in a final volume of 25 µL. The PCR mixture contained SYBR Green (Applied Biosystems, Foster City, Calif.) and 0.6 nmol of each primer (forward and reverse). The levels of transcripts were quantified using the comparative CT method relative to levels of hypoxanthine phosphoribosyltransfease (HPRT1). All samples were analyzed in triplicate wells with the median of each measurement used for CT calculations.

Gene expression analysis. Total RNA was extracted from SW620 cells transfected with siRNA NOX4_5, siRNA NOX4_8 and control siRNA 48 hr post-transfection using RNeasy Mini kit (Qiagen, Germantown, Md.), following the animal cell protocol and homogenizing via 20 gauge needles. Normal human colon RNA isolated postmortem from a donor was purchased from Ambion (Applied Biosystems, Foster City, Calif.). Nucleic acid quantity, quality and purity were determined using a Nanodrop 2000 UV-VIS spectrophotometer (Nanodrop, Rockland, Del.). cDNA was generated using the High-Capacity Reverse Transcriptase cDNA kit (Applied Biosystems, Foster City, Calif.) and 1.0 mg of total RNA according to the manufacturer's instructions. Quantitative PCR reactions were performed using the following primer sequences (Operon, Huntsville, Ala.): hypoxanthine phosphoribosyltransferase 1 (HPRT1),
HPRT1 For
5' GCCATGAAGCAGGACTCTAAAGA-3' (SEQ ID NO: 3) and
H PRT1 Rev
5'-TTGGCATAACACAGCTGATTGAT-3' (SEQ ID NO: 4);
NOX4 For
5'-ATGTCAGTTGCTGCATTCCTAA-3' (SEQ ID NO: 5) and
NOX4 Rev
5'-TCACTCAATAGTGCTGTGGTTT-3' (SEQ ID NO: 6).

EXAMPLE 3

Different Pathways Dominate Progression to Relapse in LCC and RCC

The present example demonstrates the location specificity of the dominant pathway to relapse in colon cancer. Attention is focused on samples in GSE14333 with Dukes stage A, B or C. Table 3 demonstrates the characteristics of patients in GSE14333.

TABLE 3

| | Characteristics of patients in GSE14333 | | | | |
|---|---|---|---|---|---|
| | no. | Dukes stage (A/B/C/D) | gender (M/F) | relapse in stage A, B, C (no/yes) | chemo in stage A, B, C (no/yes) |
| all tumors | 290 | 44/94/91/61 | 164/126 | 180/46 | 142/87 |
| left side | 122 | 18/37/40/27 | 77/45 | 70/23 | 55/40 |
| right side | 125 | 17/44/41/23 | 59/66 | 84/17 | 63/39 |
| Rectum | 39 | 8/12/10/9 | 26/13 | 24/6 | 22/8 |
| Other | 4 | 1/1/0/2 | 2/9 | 2/0 | 2/0 |

TABLE 4

Genes and associated pathways most significantly implicated in relapse
in left side colon cancer with Dukes stage A, B or C. Left side:

| probe | gene | CPH p-value | direction in relapse | pathways effected* | multistate marker |
|---|---|---|---|---|---|
| 236028_at | IBSP | $2.7 \times 10-5$ | UP | FA | NOX4 |
| 210095_s_at | IGFBP3 | $1.0 \times 104$ | UP | P53 | NOX4 |
| 213425 at | WNT5A | $2.5 \times 104$ | DOWN | WNT | MMP3 |
| 223121_s_at | SFRP2 | $3.1 \times 104$ | UP | WNT | NOX4 |
| 229271_x_at | COL11A1 | $7.1 \times 104$ | UP | FA | NOX4 |
| 216442_x_at | FN1 | $7.3 \times 104$ | UP | FA | NOX4 |
| 220088 at | C5AR1 | $1.4 \times 10-3$ | UP | CCC | NOX4 |
| 201109_s_at | THBS1 | $1.9 \times 10-3$ | UP | P53, TGFB, FA | NOX4 |
| 202627_s_at | SERPINE1 | $2.7 \times 103$ | UP | P53, CCC | NOX4 |
| 212607_at | AKT3 | $2.9 \times 10-3$ | UP | FA, INS | NOX4 |
| 221729 at | COL5A2 | $3.3 \times 10-3$ | UP | FA | NOX4 |
| 203083 at | THBS2 | $3.6 \times 10-3$ | UP | TGFB, FA | NOX4 |
| 204315_s_at | GTSE1 | $5.8 \times 10^{-3}$ | DOWN | P53 | MMP3 |
| 210511_s_at | INHBA | $6.2 \times 10-3$ | UP | TGFB | NOX4 |
| 202310_s_at | COL1A1 | $6.4 \times 10-3$ | UP | FA | NOX4 |
| 202833_s_at | SERPINA 1 | $6.5 \times 10-3$ | DOWN | CCC | MMP3 |

TABLE 5

Genes and associated pathways most significantly implicated in relapse in
right side colon cancer with Dukes stage A, B or C. Right side.
side colon cancer with Dukes stage A, B or C. Right side.

| | | | | | |
|---|---|---|---|---|---|
| 202267_2_at | LAMC2 | $3.7 \times 1$ e | UP | FA | CDX2 |
| 236313_at | CDKN2B | $8.9 \times 10^{-6}$ | UP | CC, TGFB | CDX2 |
| 203725 at | GADD45A | $1.7 \times 10^{-5}$ | UP | CC, P53 | CDX2 |
| 204420_at | FOSL1 | $2.0 \times 10^{-5}$ | UP | WNT | FAM69A |
| 202628_s_at | SERPINE1 | $8.7 \times 10^{-5}$ | UP | P53, CCC | CDX2 |
| 203323 at | CAV2 | $1.6 \times 10^4$ | UP | FA | CDX2 |
| 201124_at | ITGB5 | $1.7 \times 10^4$ | UP | FA | FAM69A |
| 213792_s_at | INSR | $1.8 \times 10^4$ | UP | INS | CDX2 |
| 202627_s_at | SERPINE1 | $1.9 \times 10^4$ | UP | P53, CCC | CDX2 |
| 203726 s at | LAMA3 | $2.2 \times 10^4$ | UP | FA | CDX2 |
| 208711 s at | CCND1 | $2.4 \times 10^4$ | UP | CC, P53, WNT, FA | FAM69A |
| 208613_s_at | FLNB | $3.3 \times 10^4$ | UP | FA | FAM69A |
| 201925_s_at | CD55 | $3.4 \times 10^4$ | UP | CCC | CDX2 |
| 214866 at | PLAUR | $3.4 \times 10^{-4}$ | UP | CCC | FAM69A |
| 204714_s_at | F5 | $4.7 \times 10^4$ | UP | CCC | CDX2 |
| 204363 at | F3 | $5.4 \times 10^4$ | UP | CCC | CDX2 |

*CC = cell cycle, CCC = complement and coagulation cascades, FA = focal adhesion, INS = insulin signaling, P53 = p53 signaling, TGFB = TGFI3 signaling, WNT = Wnt signaling.

Among the most significant genes in the left-side analysis is wingless-type MMTV integration site family, member 5A (WNT5A), which is down regulated in the samples that will relapse. Secreted frizzled-related protein 2 (SFRP2), which competes with the Wnt proteins for the Frizzled receptor, is up regulated. Also, the frizzled receptor, frizzled homolog 3 (FZD3), is down regulated in the relapse cases. These expression changes point to a reduction in Wnt signaling in the left-side tumors. There are no such indications in the relapse cases on the right side. Axin2 is down regulated in the relapse cases on the right side, reducing transcriptional inhibition by β-catenin.

The most striking feature of relapse on the right side is elevated expression of cyclin-dependent kinase inhibitor 2B (p15, CDKN2B), growth arrest and DNA-damage-inducible, alpha (GADD45A) and cyclin D1 (CCND1) in the relapse cases. This points to a strong proliferation signal in the right side tumors, of which there is no such indication on the left side. Genes involved in p53 signaling are altered on both sides, although more so on the right side. There are 30 probes from the selected pathways significantly implicated in relapse on both sides. These common probes are largely involved in focal adhesion, plus activity of serpin peptidase inhibitor, clade E (nexin, plasminogen activator inhibitor type 1), member 1 (SERPINE1), plasminogen activator, urokinase (PLAU) and plasminogen activator, urokinase receptor (PLAUR) in cell adhesion and migration.

EXAMPLE 4

Single Genes are Strongly Predictive of Relapse in Left-Side and Right Side Tumors and Encapsulate Pathway Activity The multistate methodology is applied separately to the left-side tumors and the right-side tumors to identify multistate probes that are significantly predictive of relapse. These panels of few genes also act as biomarkers for the pathways to progression described in the preceding section.

Figure 1B:
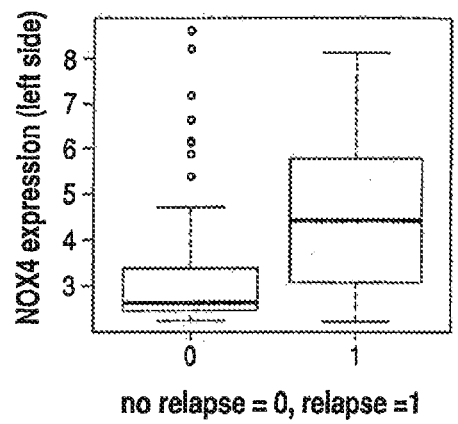
FIG. 1B. In the same set of left-side tumors, the relapse event vector gives a sample the value 0 if it is relapse-free for 60 months and the value 1 otherwise. The boxplot of NOX4 expression versus the relapse event vector illustrates the significance of the dependence.
Figure 1C:
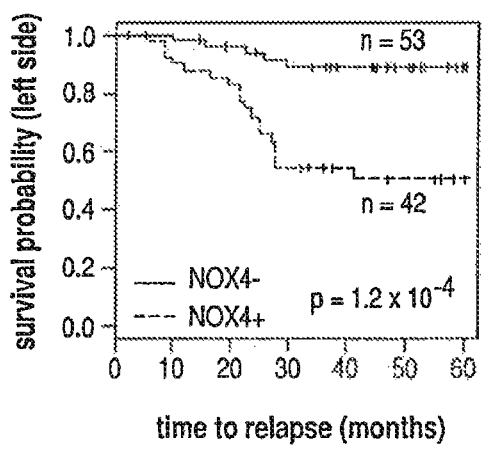
FIG. 1C. The Kaplan-Meier curves for the NOX4− and NOX4+ components plot the expected survival probabilities for the components in the left-side tumors. The 5-year expected survival probability for NOX4− is 0.89 95% CI (0.80-0.99) and for NOX4+ it is 0.51 95% CI (0.37-0.70). A Cox proportional hazard model whose only variable is an indicator for the NOX4 components has a logrank test p-value 1.2×10-4. NOX4− contains 53 samples and NOX4+ contains 42 samples.
Figure 1D:
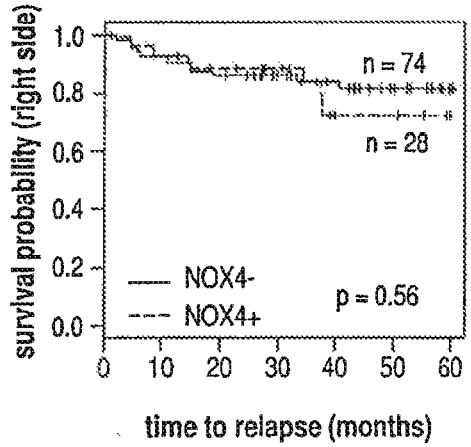
FIG. 1D. The corresponding Kaplan-Meier plots for the NOX4 components in the right-side tumors shows a distinctly lower connection with relapse than on the left side. The 5-year expected survival for NOX4− on the right side is 0.82 95C1% (0.73-0.93) and for NOX4+ it is 0.73 95% CI (0.56-0.95). On the right side only 28 samples are in NOX4+ and 72 are in NOX4−.

Application of the multistate methodology to the left-side tumors with Dukes stage A, B or C identifies 219773at (NOX4) as one of the most significant predictors of relapse. The distribution of NOX4 in the left-side tumors shows a large component with low mean expression and narrow variance, and a right tail of elevated expression (FIG. 1(a)). The multistate methodology divides the two components at the expression value 3.0. As the boxplot in FIG. 1(b) shows, there is a strong correlation between elevated NOX4 expression and relapse within 5 years. NOX4 expression is summarized as a binary variable by assigning 1 to every sample with expression level above the cut value (the NOX4+ component), and 0 for the other samples (NOX4−). (The component enriched with poor prognosis patients is assigned the value 1.) The Kaplan-Meier survival curve for the binary NOX4 variable (FIG. 1(c)) shows the prognostic power of this variable in the left-side tumors. The predictive power of NOX4 on the right-side tumors is reported in FIG. 1(d). NOX4 has a distinctly lower significance on the right side.

Low expression of the probe 206387_at (CDX2) is highly predictive of relapse in the right-side tumors (FIG. 2(b)). FIG. 2(a) illustrates the partition of the right-side samples into low (CDX2−) and high (CDX2+) components. The survival characteristics of the binary CDX2 variable in the right-side tumors and the left-side tumors are reported in FIG. 2(c,d).

In addition to NOX4, matrix metallopeptidase 3 (stromelysin 1, progelatinase) (MMP3) is a multistate gene that is predictive of relapse in left-side tumors. In this case, the low component is enriched with relapse cases. A CPH with a binary variable representing the MMP3+/− components has a p-value 3.86×10-6. NOX4 and MMP3 provide independent information about relapse since the poor prognosis components defined by the two genes have few cases in common. In the right-side tumors, the high component of family with sequence similarity 69, member A (FAM69A) is enriched with relapse cases not identified by CDX2.

In addition to separating the population of left side colon cancer disease apart from right side colon cancer disease prognosis, the multistate genes capture the pathogenic effects of the genes listed in Table 4 and Table 5 hence, the pathways containing these genes. For example, the most significant gene in the left-side analysis is integrin-binding sialoprotein (IBSP). The NOX4+ component, in addition to containing the samples with elevated NOX4 expression contain the samples with elevated IBSP expression. Assessing the relationship quantitatively, a t-test for the mean expression value of IBSP in NOX4+ versus NOX4− has a p-value of $1.38 \times 10^{-5}$. A CPH using IBSP expression as the variable, restricted to NOX4−, is not statistically significant, since the NOX4− component contains almost no samples with elevated expression of IBSP. In this way, IBSP can be replaced by NOX4 in a survival model. The multistate gene MMP3 similarly represents the next most significant gene, WNT5A. In Table 4 and Table 5, for each probe, the multistate gene is identified that separates the gene's expression into high and low components in a statistically significant manner On the right side, CDX2 effectively represents almost all of the probes listed in Table 5.

Tests that monitor only NOX4 would not be capable of distinguishing LCC from RCC disease. The ability to distinguish LCC from RCC disease is possible here because of measuring expression levels of CDX2. The inclusion of additional probes for CDX2 and/or FAM69A, as identified in Table 5, provides a much more robust analysis, and corrects an otherwise incorrect diagnosis of a colon cancer patient as at "low risk" for recurrent colon cancer relapse. Specifically, because patients with RCC do not have low expression levels of NOX4, (below normal, non-cancerous tumor tissue), such patient tissue samples would be erroneously identified as "good prognosis" patients, with a good indication of colon cancer free survival. Only by first being able to identify a patient as having RCC rather than LCC disease, and then taking the next step of examining these right side colon tumor patient tissue for expression of, especially CDX2, can otherwise false negative (false "good prognosis") patients be identified and proper clinical protocol be determined.

For patients with RCC disease, this test is especially critical, and provides an entirely new prognostic tool, especially since NOX4 is not among the genes found to be differentially expressed in this pathology. Genetic probes for NOX4 are therefore of little to no utility in the accurate prognosis on RCC. Tests that only measure NOX4 expression would be incapable of accurately identifying poor prognosis patients that may have right-side or left-side disease. For a set of LCC samples, 89% of the patients identified as good prognosis by NOX4 will be free of relapse for 5 years (legend of FIG. 1(c)), resulting in an about 11% misclassification rate. However, for a set of RCC samples, 82% of the patients identified as good prognosis by NOX4 will be free of relapse for 5 years (legend of FIG. 1(d)), meaning a higher percentage, about 18%, are misclassified as good prognosis, and contrary to an initial good prognosis, later relapse. On the other hand, if CDX2 is used as a prognostic test for RCC samples, the misclassification rate is only 12% (legend of FIG. 2(c)). Thus, viewing these results over both LCC and RCC, using only NOX4 as a prognostic test, a false identification rate of 14.5% exists among the samples characterized as good prognosis. A test that uses NOX4 for LCC samples and CDX2 for RCC samples has a much lower misclassification rate of 11.5%. This is a statistically and medically significant improvement in prognostic power.

EXAMPLE 5

NOX4 mRNA Interference with siRNA in Colon Cancer (SW620) Cells Reduces Superoxide Production Levels without Affecting Cell Viability The present example demonstrates the utility of the present invention for treating left-side colon cancer disease through targeted reduction of colon cancer cell superoxide production. Because elevated NOX4 is identified as being prognostic of a high probability of colon cancer disease relapse in left colon cancer disease, it is proposed that this model may be used to identify and screen for pharmaceutical agents useful in the improved treatment of patients identified to have left-side colon cancer disease.

Overproduction of reactive oxidative species (ROS) has long been recognized as a risk factor in carcinogenesis. To further investigate NOX4 function in colon cancer, superoxide production was measured by the chemiluminescent method for SW620 cells. SW620 cells are a lymph-node metastasis colon adenocarcinoma cell line. NOX4 is shown to be expressed in this cell line, and the present example demonstrates that application of NOX4 siRNA causes a significant reduction in ROS production.

Figure 5:
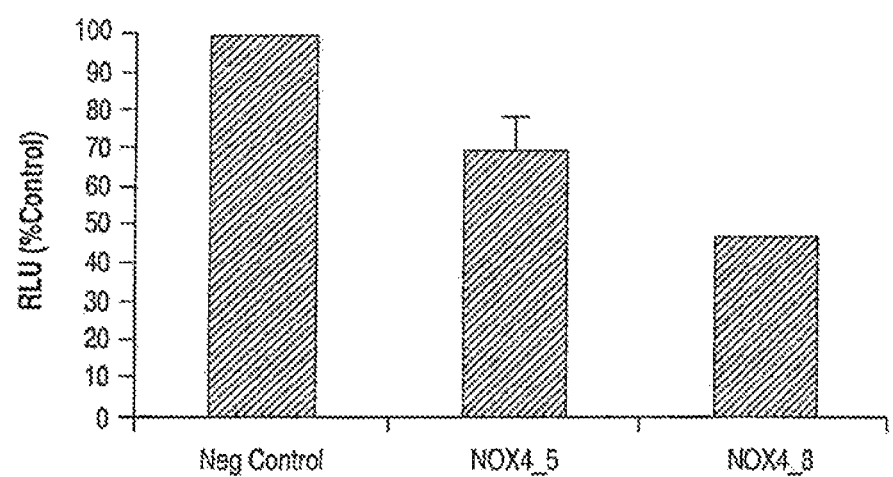
FIG. 5. Targeted NOX4 knockdown decreases superoxide production in SW620 cells. SW620 cells were transfected with NOX4 siRNA and assayed for superoxide production by the chemiluminescent method. Superoxide producing activity of AllStar negative siRNA transfected cells are set as 100%. Each bar represents the mean data from 2 independent transfections, with error bars representing the S.D. for percentage of activity.
Figure 6:
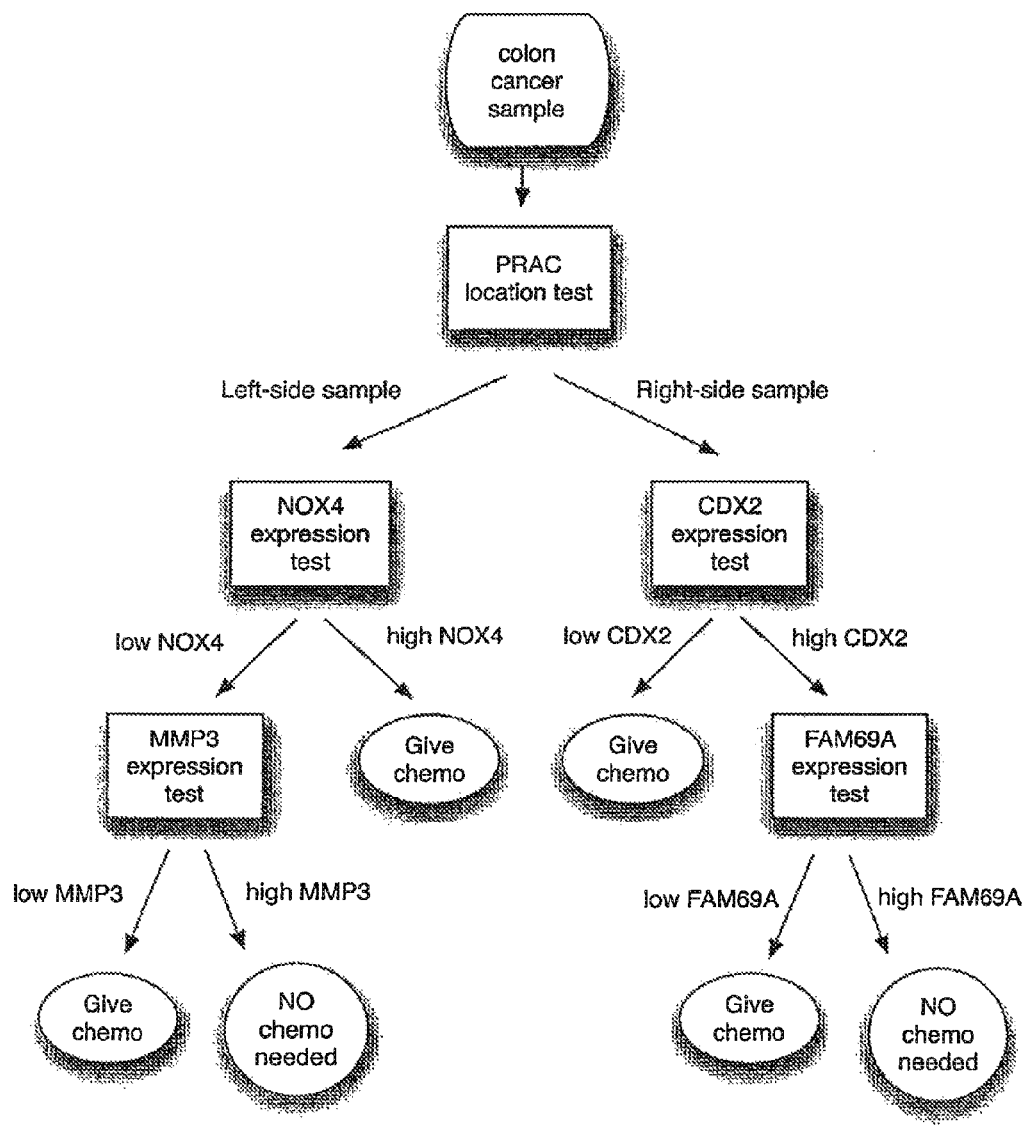
FIG. 6. Flow chart of screening a colon cancer patient. This flow chart may be embodied as a software program that may be used in an automated clinical tool for screening patient samples. As shown, the left-side colon cancer expression panel excludes CDX2, and the right-side colon cancer panel test excludes NOX4.

Expression of NOX4 (mRNA levels) was examined in four cell lines: HT29, HCT 116, SW480 and SW620, the patient-matched lymph-node metastasis to SW480 (Dukes stage B). NOX4 inhibition with RNA interference in SW620 cells was found to be associated with a decrease in superoxide producing activities of the cells as indicated by the reduced ROS production (FIG. 5).

Cell lines derived from primary adenocarcinoma or carcinoma colon tumors (HCT116, HT29 and SW480) were found to have NOX4 expression levels below or comparable to normal, non-cancerous colon NOX4 levels. However, NOX4 expression was found to be greatly elevated in an adenocarcinoma cell line SW620 compared to normal colon (See FIG. 3). The adenocarinoma cell line SW620 was derived from the lymph metastatic site (SW620).

Figure 4A:
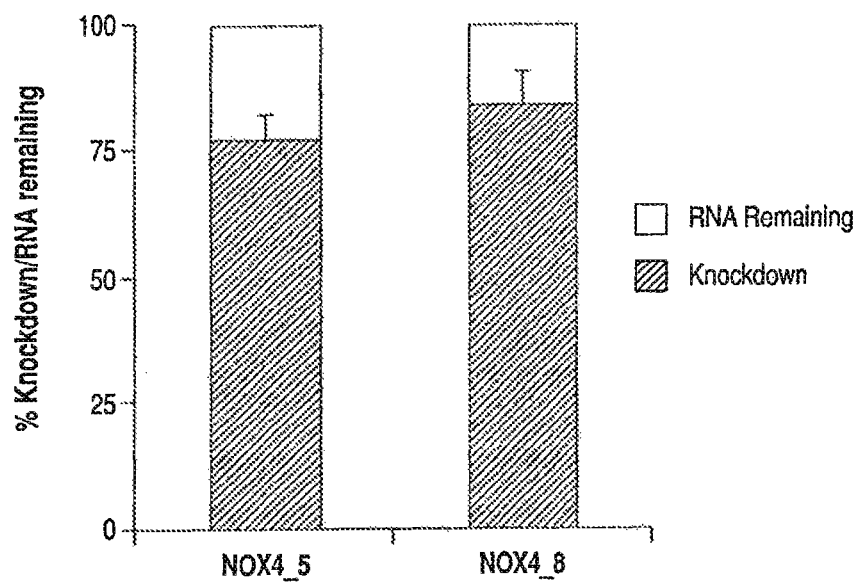
FIG. 4A. siRNA suppression of NOX4 does not affect SW620 cell viability. RTPCR results showing transfection with NOX4 siRNA reduces NOX4 mRNA levels in SW620 cells compared with control AllStar negative siRNA. A positive control AllStar Death siRNA was also used to validate transfection efficiency (data not shown).
Figure 4B:
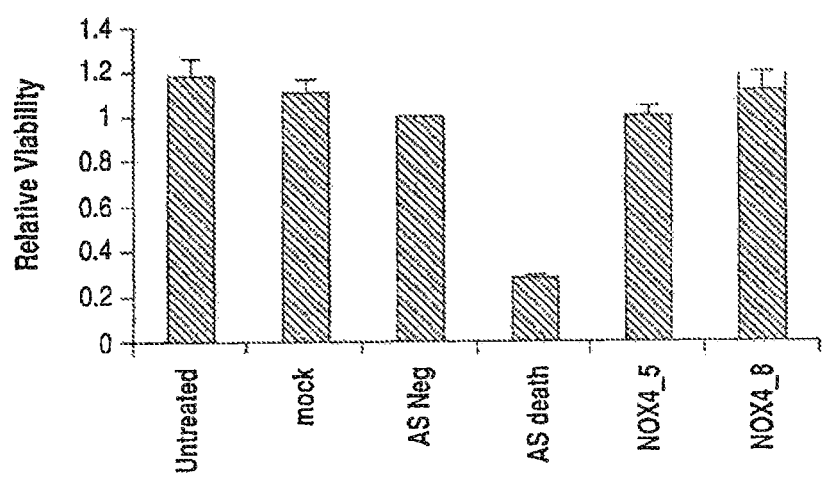
FIG. 4B. Cell viability was normalized to AllStar negative transfected SW620 cells. NOX4 siRNA and AllStar negative siRNA transfected SW620 cell have similar cell viability. Assays were performed in triplicate. Similar results were obtained in two separate experiments.

To investigate NOX4 function in metastatic SW620 cells, the affect of NOX4 on cell viability was examined. NOX4 expression was silenced using RNAi interference by transfecting SW620 cells with oligonucleotides targeting the NOX4 transcript. Similar cell viability was observed between NOX4 silenced cells and negative control cells as reported in FIG. 4. Therefore, targeted NOX4 knockdown does not seem to affect cell viability.

To further investigate NOX4 function in SW620 cells, superoxide production was assayed by the chemiluminescent method. NOX4 inhibition with RNA interference in these SW620 cells was found to be associated with a decrease in superoxide producing activities of the cells, as indicated by the reduced ROS production (FIG. 5).

EXAMPLE 6

Left-Side Colon Careinogenesis and Disease Progression and Right Side Colon Carcinoenesis and Disease Progression The microarray dataset GSE14333 analyzed here demonstrates that disease progression in RCC is dominated by elevated Wnt signaling and elevated proliferation, most strongly indicated by elevated levels of CCND1 in the relapse cases. Up regulation of CCND1 is accompanied by increased expression of the pro-apoptotic gene GADD45,4 and elevation of the growth arrest gene CDKN2B. Thus, these tumors that have not yet metastasized may be in a cycle of rapid mitosis and apoptosis. The GSE14333 dataset is different from other datasets, such as GSE12945, GSE17536, GSE17537. The cohort GSE14333 contains the patients in GSE17536, GSE17537, but it also contains samples not studied earlier.

In LCC progression to relapse is characterized by reduced Wnt signaling and, paradoxically, elevated expression of the anti-angiogenic genes thrombospondin 1 (THBS1) and SERPINEL The data present fewer clear indications of the route to relapse in LCC.

In a pancreatic cancer cell line, inhibition of NOX4 activates apoptosis via the AKT-ASK1 cell survival pathway[19]. In the present example, NOX4 inhibition in SW620 shows no decrease in cell viability. However, reduction of NOX4 expression via siRNA-mediation corresponds to a significant reduction in ROS production in the SW620 cells. This finding suggests that NOX4 is a novel source of ROS production in metastatic and pre-metastatic colon cancer.

Figure 3:
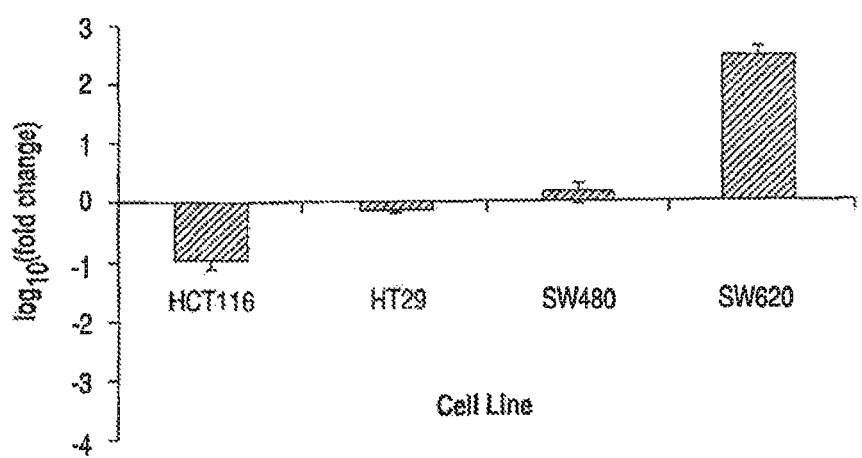
FIG. 3. Expression of endogenous NOX4 in human colon cancer cell lines. RTPCR was performed using RNA from several human colon cancer cell lines (HCT116, HT29, SW480 and SW620) with specific primers for NOX4. NOX4 mRNA levels were quantified using the comparative CT method relative to levels of hypoxanthine phosphoribosyltransfease (HPRT). The fold change in expression (Logio) was normalized to normal colon NOX4 mRNA levels. Three experiments were conducted in triplicate. Bars represent the median fold change (Logio) and the error bars represent the standard deviation.

From this data, it is reasoned that if NOX4 exerts cancer-promoting effects, it is most likely at more advanced tumor stages, as NOX4 expression is comparable to normal colon levels in primary adenocarcinoma and carcinoma derived cell lines and above normal colon levels in the metastatic cell line, SW620 (FIG. 3).

In renal cell carcinoma, NOX4 is critical for HIF2-alpha transcriptional activity[20]. Specifically, inhibition of NOX4 decreases HIF2-alpha production. In the left-side colon cancer samples microarray data, there was no change in HIF2-alpha expression between the NOX4- and NOX4+ component. A change in hypoxia-related gene expression that was identified was a small decrease in HIG1 hypoxia inducible domain family, member 1 A and HIG1 hypoxia inducible domain family, member 2A expression in NOX4+ over NOX4-. The results in Table 4 show that NOX4 expression is central to the progression of LCC.

Low expression of MMP3 is also implicated in left-side colon cancer disease progression. MMP3 is a member of the matrix metalloproteinases family of extracellular proteinases that mediate many of the changes in the tumor microenvironment during cancer progression[26]. The genes correlated to MMP3 in expression (see Table 4) point to a significant role for reduced Wnt signaling in left-side disease progression. WNT5A is a known tumor-suppressor whose promoter is frequently methylated in colorectal cancer21. In contrast, Wnt signaling is apparently elevated in the right-side colon cancer relapse cases.

In RCC, low expression of CDX2 is strongly associated with relapse. CDX2 acts as a transcription factor, initially expressed during embryogenesis in the development of the small intestine and colon, and regulating a diverse range of functions from proliferation, cell-cycle arrest, differentiation, and apoptosis[22]. In healthy adult colon tissue, CDX2 is expressed throughout the colon and regulated post-transnationally through phosphorylation. With carcinogenesis, expression patterns of CDX2 are altered. Analysis of 65 colorectal tumors mapping CDX2 expression throughout the colon and rectum found significantly lower expression of CDX2 in 37 right-sided, poorly differentiated tumors as compared to 28 left-sided tumors[23]. Methylation of the CDX2 promoter has been proposed as a mechanism for down-regulation in colorectal carcinomas[24]. CDX2 inhibits the Wnt signaling pathway, through reduction of the tyrosine phosphorylation of 13-Catenin, resulting in decreased T-cell factor signaling and cell proliferation[27]. With the reduced expression of CDX2 that accompanies carcinoma, it has been described as functioning in a tumor-suppressor role. In addition, CDX2 regulates E-cadherin trafficking to the cell membrane[28].

FAM69A is located at 1p22.1, a genomic region that is preferentially deleted in microsatellite stable colon tumors25. A locus of genes in this region, including FAM69A, contains single nucleotide polymorphisms that increase the risk of multiple sclerosis29. Expression patterns of the genes in this region do not show signs of deletion in the microarray data used here. The mechanism by which FAM69A expression is correlated with relapse risk remains an open problem for future study.

It has previously been proposed that the differences in survival between RCC and LCC could be the results of any number of causes, for example difference in time of detection, embryologic origin, exposure to fecal matter or genetics3. Regardless of the underlying cause, different mechanisms dominate progression of RCC and LCC, establishing that they should be treated as different diseases. The prominent role of NOX4 as a prognostic biomarker in LCC makes it a important target for this cancer biology and LCC specific therapeutics.

EXAMPLE 7

Genomic Test for Separating Right-Side Colon Cancer (RCC) from Left Side Colon Cancer (LCC) with a High Degree of Accuracy Expression levels of the gene prostate cancer susceptibility candidate (PRAC) can be used to accurately estimate the location of origin of a colon tissue sample. Using microarray data from GSE14333 and the array probe 230784_at for PRAC, 91% of right-side colon samples are shown to have negligible expression levels of PRAC, while 79% of left-side colon samples have positive expression levels of PRAC.

As used herein, a positive expression level of a gene, such as PRAC, is defined as having a detectable expression level by quantitative RT-PCR. A negligible expression level of a gene, such as PRAC, is defined as not having a detectable level of expression by quantitative RT-PCR.

A colon tumor sample that positively expresses the gene PRAC is very likely to be a left-side sample. A colon tumor sample that has negligible expression of the gene PRAC is very likely to be a right-side sample.

PROPHETIC EXAMPLE 8

RCC and LCC Proamaosti Colon Cancer Test for Clinical Use with FFPE Specimens

Common practice in clinical pathology is to preserve a solid tumor tissue sample in formalin and fix it in paraffin. This sample is examined under a microscope in the process of establishing the tumor stage and it is readily available for staining with protein antibodies or analysis of DNA. Any widely used diagnostic test using colon tumor samples must be applicable to formalin-fixed, paraffin-embedded (FFPE) tissue.

Translating a genomic prognostic test developed with microarrays to one that uses FFPE tissue faces the following difficulty. Fixing tissue in formalin is known to degrade some species of mRNA. For this reason, analyses that measure the entire genome of mRNA species, such as microarray analysis with AFFYMETRIX GENECHIP arrays, require frozen tissue samples. The analysis of microarray data that lead to the prognostic tests in this invention used frozen tissue samples. If two samples recovered from the same tissue block, one frozen and one prepared as an FFPE block, are hybridized to whole-genome microarray, some of the mRNA species will produce equivalent readings on both arrays and others will show significantly reduced levels in the sample from FFPE tissue.

The prognostic tests for LCC and RCC disclosed in this invention uses one or more gene in its several embodiments, however, no increased prognostic power is found with more than two genes. The efficient method for measuring the expression levels of few genes is quantitative RT-PCR. Thus, one version of the test that could be used in a clinical setting will use RT-PCR to measure several species in mRNA from an FFPE tissue source. Because some mRNA species may be degraded in FFPE tissue, alternative tests will be sought using probes found in Table 1 and Table 2. This development process proceeds through the following two steps, separately for LCC and RCC.

For each mRNA species in Table 1 and Table 2, look for RT-PCR probes that yield equivalent measurement of the mRNA species in frozen and FFPE preparations of the same colon tissue. The identification of an RT-PCR probe is known to one skilled in the art of molecular biology. The RT-PCR probe is an oligonucleotide of 15-60 nucleotides that hybridize with high specificity to the targeted species of mRNA.

From the subset of genes in Table 1 and Table 2 for which the first step was successful, develop a prognostic panel by the following procedure. Using a test set of FFPE colon cancer samples (RCC and LCC respectively) with known 5-year relapse status, select as the first gene in the panel the one that is most significantly prognostic. From the remaining genes, select the one such that the intersection of its good prognosis component with the good prognosis component of the first gene, is most significantly prognostic among the alternatives. This process is continued until further intersection with good prognosis components no longer increases the prognostic significance.

EXAMPLE 9

Computer Methods for Determining Relapse and Relapse Free Probability in Colon Cancer Patients and Chemotherapy Responsiveness The present example is provided to demonstrate the utility of the present method as a computerized method that may be used in the practice of the invention.

Computerized Method for Determination of Relapse/Non-Relapse in an LCC or RCC Patient Population:

In another aspect, the invention provides a computer implemented method of determining relapse free survival probability for a LLC or RCC patient having undergone colon cancer surgery. In one embodiment, the computerized method comprises classifying the colon cancer patient as a right side colon cancer (RCC) or as a left side colon cancer (LCC) disease patient by identifying the side of the colon on which the colon cancer was localized and providing said identifying classification to a receiver module, where the identifying classification of the patient is LCC disease, measuring an expression level of an RNA transcript or expression product of NOX4 in a colon cancer tissue obtained from the LCC patient, to provide a test NOX4 test level, and where the identifying classification of the patient is RCC disease, measuring an expression level of an RNA transcript or expression product of CDX2 in a colon cancer tissue obtained from the RCC patient, to provide a test CDX2 level, and providing said expression level data to a receiver module; and determining the relapse free survival probability of the LCC patient as good in a LCC patient tissue with a low NOX4 expression level, and a relapse-free survival probability to a LCC patient as poor with a high NOX4 expression level, and determining the relapse-free survival probability of an RCC patient as poor in a RCC patient tissue with a low CDX2 expression level, and a relapse-free survival probability as good with a high CDX2 expression level, wherein an expression level is considered low or high as compared to a threshold value, wherein said threshold value is calculated from a reference set of like-gene expression levels from a like-classified colon cancer patient population, said like-classified patient population comprising relapse and relapse-free colon cancer patients.

In some embodiments, the method may further include a computer implemented step wherein the module is directed to generate a prognosis report of said LCC patient or RCC patient.

Computerized Method for Determination of Responsiveness or Lack of Responsiveness to Chemotherapy in an LCC or RCC Patient Population:

In another aspect, the some embodiments, the invention provides a computer implemented method of determining the probability that a LCC or RCC patient will not be responsive to chemotherapy. In patients determined to have a low probability of being responsive to chemotherapy, the patient may be excused from chemotherapy after having undergone colon cancer surgery.

In one embodiment, the computer implemented method of determining a probability of a lack of responsiveness to chemotherapy treatment in a patient having had surgical intervention for right side colon cancer (RCC) or left side colon cancer (LCC), comprises classifying the colon cancer patient as a right side colon cancer (RCC) or as a left side colon cancer (LCC) disease patient by identifying the side of the colon on which the colon cancer was localized and providing said identifying classification to a receiver module, where the classification of the patient is LCC disease, measuring an expression level of an RNA transcript or expression product of NOX4 in a colon cancer tissue obtained from the LCC patient, to provide a test NOX4 test level, and where the identifying classification of the patient is RCC disease, measuring an expression level of an RNA transcript or expression product of CDX2 in a colon cancer tissue obtained from the RCC patient, to provide a test CDX2 level, and providing said expression level data to a receiver module; and determining the likelihood of response to chemotherapy of the LCC patient as low in a patient with a low NOX4 expression level; and determining the likelihood of response to chemotherapy of the RCC patient as low in a patient with a high CDX2 expression level.

As part of this method, an expression level is considered low or high as compared to a threshold value, wherein said threshold value is calculated from a reference set of like-gene expression levels from a like-classified colon cancer patient population, said like-classified patient population comprising relapse and relapse-free colon cancer patients not having received chemotherapy.

In some embodiments, the method may further include a computer implemented step wherein the module is directed to generate a prognosis report of said LCC patient or RCC patient.

EXAMPLE 10

Prognostic Probes and Development Thereof for RCC and LCC

The various probes identified in Tables 2, 3, 4 and 5 were employed in the various examples provided here, and found to render robust and highly prognostic data concerning colon cancer relapse, survival probabilities and expected likelihood of favorable response to chemotherapy. In some embodiments, the particular gene probes used are provided in Table 6. These particular probes are commercially available.

TABLE 6

Probes

LEFT-SIDE Probes

| | | | | |
|---|---|---|---|---|
| 205828_at | MMP3 | NM002422 | #1 | GAAAATCGATGCAGCCATTTCTGAT |
| | | | #2 | TTTATTTCTTTACTGGATCTTCACA |
| | | | #3 | GATCTTCACAGTTGGAGTTTGACCC |
| | | | #4 | TAATTCTTCACCTAAGTCTCTGTGA |
| | | | #5 | ATTGAAATGTTCGTTTTCTCCTGCC |
| | | | #6 | GTGACTCGAGTCACACTCAAGGGAA |
| | | | #7 | TGAGCGTGAATCTGTATCTTGCCGG |
| | | | #8 | GTATCTTGCCGGTCA 11111 ATGTT |
| | | | #9 | CAAATGGGCTGCTGCTTAGCTTGCA |
| | | | #10 | TTAGCTTGCACCTTGTCACATAGAG |
| | | | #11 | GGGGAAGCACTCGTGTGCAACAGAC |
| 230748_at | SLC16A6 | A1873273 | #1 | GGTTACAGGTACACACAAGCTTGAA |
| | | | #2 | TGTAGAGCATCTTATCAGCCATAGA |
| | | | #3 | GGATGTAGCAAATCTCTGTCACTGC |
| | | | #4 | CTCTGTCACTGCTTGAGAACTTTGA |
| | | | #5 | GAGCTTGTGG CAGTTTTGCAGACTT |
| | | | #6 | GACTTACATGACTTCAGCACTTTAC |
| | | | #7 | AGCACTTTACGACATATTTTTACT |
| | | | #8 | ACTGATTTCTGAGGGATCTGCTCCA |
| | | | #9 | ATCTGCTCCATGTCTATTCTGTTAT |
| | | | #10 | GTATGCCAATTTCAGTATGTCAATA |
| | | | #11 | GACATTCTGGTACTTCTAGATTTGC |
| 205990_s_at | WNT5A | NM_003392 | #1 | ATCACCTCAGCCAACTGTGGCTCTT |
| | | | #2 | CAACTGTGGCTCTTAATTTATTGCA |
| | | | #3 | GCATAATGATATTCACATCCCCTCA |
| | | | #4 | ACATCCCCTCAGTTGCAGTGAATTG |
| | | | #5 | GATTGTTCCTTTTTAGTGACTCATG |
| | | | #6 | GTTGAGTTTAACAATCCTAGCTTTT |
| | | | #7 | AAATATTCTACATGTCATTCAGATA |
| | | | #8 | ATTATGTATATCTTCTAGCCTTTAT |
| | | | #9 | ATCTTCTAGCCTTTATTCTGTACTT |
| | | | #10 | ACATATTTCTGTCTTGCGTGATTTG |
| | | | #11 | GCGTGATTTGTATATTTCACTGGTT |
| 202435_s_at | CYP1 B1 | AU 154504 | #1 | GAGTCAAAGACTTAAAGGGCCCAAT |
| | | | #2 | ACATACTGCATCTTGGTTATTTCTG |
| | | | #3 | TCTGAAGGTAGCATTCTTTGGAGTT |
| | | | #4 | CCCAAACACTTACACCAAACTACTG |
| | | | #5 | TGGTAACCAGGCCATTTTTGGTGGG |
| | | | #6 | GGGAATCCAAGATTGGTCTCCCATA |
| | | | #7 | GATTGGTCTCCCATATGCAGAAATA |
| | | | #8 | TAGACTCTAGTATTTATGGGTGGAT |
| | | | #9 | ATCCTTTTGCCTTCTGGTATACTTC |
| | | | #10 | ACTCCAAGGTGATGTIGTACCICTT |
| | | | #11 | GTACCTCTTTTGCTTGCCAAAGTAC |

TABLE 6-continued

Probes

| | | | | |
|---|---|---|---|---|
| 219773_at | NOX4 | NM_016931 | #1 | TATAGGACGTCCTCGGTGGAAACTT |
| | | | #2 | GTGTTTTCTGTTGTGGACCCAATTC |
| | | | #3 | CCCAATTCACTATCCAAGACTCTTC |
| | | | #4 | AACTTTTGCCATGAAGCAGGACTCT |
| | | | #5 | GGAATCAATCAGCTGTGTTATGCCA |
| | | | #6 | GTGGCAACATGACCGTCACATTACA |
| | | | #7 | GATGCACACTGTTGATTTTCATGGT |
| | | | #8 | ATGGTGGATTCAAGAACTCCCTAGT |
| | | | #9 | AGCTGAACTTGCTCAATCTAAGGCT |
| | | | #10 | TAAGGCTGATTGTCGTGTTCCTCTT |
| | | | #11 | TGTCGTGTTCCTCTTTAAATTGTTT |
| 236028_at | IBSP | BE466675 | #1 | GAAGTTCAACTCAGGAAGGTGCAAT |
| | | | #2 | GTACTACCGTTCCAGATTTCTGTA |
| | | | #3 | CAAAGTAATAGGCTICTTGTCCCIT |
| | | | #4 | CCCTTTTTTCTGGCATGTTATGG |
| | | | #5 | TTATCAAGCAGTACACCAACTCATA |
| | | | #6 | ATAGTAGAACATGCCTGTAG |
| | | | #7 | ATGCCTGTAGTATTGCTAACTGCAA |
| | | | #8 | AGTTTCTTAATCGCACTACCTATGC |
| | | | #9 | CGCACTACCTATGCAACACTGTGTA |
| | | | #10 | ACACTGTGTATTAGGTTTATCATCC |
| | | | #11 | GTGACCTGTATGTATATTCTAATCT |
| U85658 | TFAP2C | U85658 | #3 | AG CAATTTGTTG CTGCTTGTCACCC |
| | | | #4 | CAAGTCCCCGTGGAGGTTCTGTATT |
| | | | #5 | GAAACAGTGCGTTGAGTGTACAGAT |
| | | | #6 | GGGTCTGTAAATACTGGTGCACTTC |
| | | | #7 | ATGCCTGTAGTATTGCTAACTGCAA |
| | | | #8 | CAATAACTTTGTCTCGTTCCTGTTG |
| | | | #9 | GTTCCTGTTGGGCTGAACCCTAAGG |
| | | | #10 | TTGGAATTGAACTCTCTGCCTGTAA |
| | | | #11 | AATGTTCCCAAATAATTGTTGTGT |
| 206091_at | MATN3 | NM_002381 | #1 | TTTGCTTATTTTGTTGGAGTATTA |
| | | | #2 | AAGTGAACATTACTTGCCATTTT |
| | | | #3 | ATTTTGCTTCAGGATCCAAGTGACA |
| | | | #4 | GTCTTTTTAATGTTAGTGATCCACC |
| | | | #5 | GATTACAGGCTTGAAAGTCTAACTT |
| | | | #6 | TTGATACATATAATTCTTTTGGCTT |
| | | | #7 | TGCACTGCTCAATTCTGTTTTTCGT |
| | | | #8 | TCTGTTTTTCGTTTGCATTGTCTTT |
| | | | #9 | TTACCTTTACATATTATCATGTCTA |
| | | | #10 | TCATGTCTATTTTTGATGACTCATC |
| | | | #11 | GATGACTCATCAATTTGTCTATTA |
| 204672_s_at | ANKRD6 | NM_014942 | #1 | ACAGAACAGGCTCAGTCAGCATCCT |
| | | | #2 | AGCATCCTCACCCAG GATGGCAAC |
| | | | #3 | GGCAACATCTATTAAGACCAATGCA |
| | | | #4 | GACCAATG CAATACCTTTTCATCTT |
| | | | #5 | ATACCTTTTCATCTTCAGCAAATGT |
| | | | #6 | TGATCCTTG G CATTGTCAA |
| | | | #7 | G GTCCAGTGTATACCTTATT |
| | | | #8 | TTTTCCCTTTTAGCTATCTGCTAAA |
| | | | #9 | AAATGCCACAACTGTACIHICCAA |
| | | | #10 | TGACAACTTATAGCCTGTCATGCAG |
| | | | #11 | GCAGGTCATGTTTCAAATCAAGGCT |

RIGHT-SIDE PROBES

| | | | | |
|---|---|---|---|---|
| 216044_C_at | FAM69A | AK027146 | #1 | TATACACCCATTTTTAACCTCATTT |
| | | | #2 | CAAAGGGCCCATCTTAGTATCACGC |
| | | | #3 | TAGTATCACGCAG CTGACTGAGCCC |
| | | | #4 | GACTGAGCCCTTCAAAACTGACATC |
| | | | #5 | AAAACTG ACATCTTAAGGCCCAATC |
| | | | #6 | AGGCCCAATCAAGATCCACATATCC |
| | | | #7 | GTATATCCTGTGGGCCAAAGGGCTA |
| | | | #8 | TATCTAATGTTTTTTTCCCCATGTA |
| | | | #9 | TTAGTATTTGCTCCTCTTTCATATT |
| | | | #10 | TTCACACGTATACTCAGATTTGGCA |
| | | | #11 | TGGCATGTACCTTTCAACATCTCCA |

TABLE 6-continued

| | | | Probes | |
|---|---|---|---|---|
| 206387_at | CDX2 | 751096 | #1 | GACAAGTGGGATTTGGGGCCTCAAG |
| | | | #2 | GGGCCTCAAGAAATATACTCTCCCA |
| | | | #4 | GGCTTCATTCCGGACTGGCAGAAGC |
| | | | #8 | TGACCAAAGACTGCAGAACCCCCAG |
| | | | #9 | GAGGGGGTGGTTATTGGACTCCAGG |
| | | | #11 | TAGAGAGCCTGTCACCAGAGCTTCT |
| 225582_at | ITPRIP | AA425726 | #1 | CTCGGCTGTGATCAGGGCAACCAAA |
| | | | #2 | TTAGACTGAACATGTGCTTGGGCCT |
| | | | #3 | CTCTCCCTAGACGCAGTTGCGGGGC |
| | | | #4 | TGCGGGCACTCCAGGGAATGAACC |
| | | | #5 | ATGAACCAGCTCAAGTGTGTCCCTA |
| | | | #6 | CCTCCTCATTCCATCAGATGCATTT |
| | | | #7 | TGCTTTGAAGAGACCCCAGTAACCA |
| | | | #8 | AAGCCAAAACCATGCCTGGATCTCC |
| | | | #9 | ATCTTCTGGCTTCTTGTGTGTACAG |
| | | | #10 | GAATCTTTTTCTGCACCAAAGCTG CT |
| | | | #11 | GGTGTTTCATGCTGCCTTATTTATA |
| 201474_s_at | ITGA3 | NM_002204 | #1 | GCCACAGACTGAACTCGCAGGGAGT |
| | | | #2 | GCAAACGGCAACGTAGCCTGGGCTC |
| | | | #3 | ATGGCGGGATCCTCCACAGAGAGGA |
| | | | #4 | AGCCTCCAGAAGGCCCCAGAGAGAC |
| | | | #5 | GACCCTGCAAGACCACGGAGGGAGC |
| | | | #6 | GGAGGGAGCCGACACTTGAATGTAG |
| | | | #7 | CCAGCTGAACCATGCGTCAGGGGCC |
| | | | #8 | GTCAGGGGCCTAGAGGTGGAGTTCT |
| | | | #9 | GTGGAGTTCTTAGCTATCCTMGCT |
| | | | #10 | GTGTCCTAAGGCCCATTTGAGAAGC |
| | | | #11 | AGGCTAGTTCCAAAAACCTCTCCTG |
| 225667_s_at | FAM84A | AI601101 | #1 | ATAGCATCTATGTCTCTTTCAAGGG |
| | | | #2 | GACAGCAAGTATTATGG CCAAAG CC |
| | | | #3 | AAAGCCAGTTTCTTGGCATTTCAAA |
| | | | #4 | TGGTTTTTCATCCTGGATTCATCCCC |
| | | | #5 | GGATTCATCCCCTGATCTTAAATCA |
| | | | #6 | TAATAACTAACTTACCTTTGCATGT |
| | | | #7 | AACTTACTCCTCTTTCAAGTAACAG |
| | | | #8 | TATTGTATCTACACACTCCACATTC |
| | | | #9 | CATTCTTTACTGTGTCCTACTACTG |
| | | | #10 | TGTGTCCTACTACTGTATCTTG G CT |
| | | | #11 | TCTTGGCTCCCTGCTGTATTAAACA |
| 227123_at | RAB3B | AU156710 | #1 | GAGGCTTCCCTCAGATCAAGGAGCC |
| | | | #2 | G CAGATGATCTATCTCTGTGG CCAC |
| | | | #3 | GAGATGTCACCTTATGCAATTTGCA |
| | | | #4 | TGCATATCATATTCAATTCCCCCAA |
| | | | #5 | CCCAACTGCTCTTTCTAATTTATTC |
| | | | #6 | ATTCAACTGGGGACCAGGCTGGTCT |
| | | | #7 | TGGTCTCATGCCAACCTAGGAGATG |
| | | | #8 | TGCAGTTGCCTCTCGATAGGCCTGA |
| | | | #9 | GAGGAACAATAGCTCTCACGTCTCT |
| | | | #10 | TCTCCTCATCAGATTTTAACTAAGC |
| | | | #11 | ATCTATGGTGTTTCCTTGTTCTGTG |
| 218284_at | SMAD3 | NM_015400 | #1 | GGTGTAGTGGCTTTTTGGCTCAGCA |
| | | | #2 | GGCTCAGCATCCAGAAACACCAAAC |
| | | | #3 | GGCTGG CTAAACAAGTGGCCG CGTG |
| | | | #4 | CAG CTCTGAGTCAAATCTGGG CCCT |
| | | | #5 | CCCACTCCCTTGCTAGGGGTGAAAG |
| | | | #6 | GAGCCATCTATCCAAGAAGCCTTCA |
| | | | #7 | CTGTTCTGGACTCTGATGTGTGTGG |
| | | | #8 | GCCAGCCTGACCTTTTAATAACTTT |
| | | | #9 | GCACCTGTTTAAGCATTGTACCCCT |
| | | | #10 | GTTAAAGATTTGTGTCCTCTCATTC |
| | | | #11 | TCCTCTTGTAAGTGCCCTTCTAATA |
| 205559_s_at | PCSK5 | NM_006200 | #1 | GCAACGAAGAGTCCTGGGCGGAAG |
| | | | #2 | GAGTCCTGGGCGGAAGGAGGCTTCT |
| | | | #3 | GAAGGAGGCTTCTGTATGCTTGTGA |
| | | | #4 | GAGGCTTCTGTATGCTTGTGAAAAA |
| | | | #5 | GAAAAAGAACAATCTGTGCCAACGG |

TABLE 6-continued

| | | | | Probes |
|---|---|---|---|---|
| | | | #6 | AATCTGTGCCAACGGAAGGTTCTTC |
| | | | #7 | TGTGCCAACGGAAGGTTCTTCAACA |
| | | | #8 | ATTTCAAGGCTGAGCAGCCATCTTA |
| | | | #9 | GGCTGAGCAGCCATCTTAGATTTCT |
| | | | #10 | GAGCAGCCATCTTAGATTTCTTTGT |
| | | | #11 | ATTTCTTTGTTCCTGGACTTATA |
| 219909_a | MMP28 | NM_024302 | #1 | CCTTTGTTCCTTGAAGAATGCAGCA |
| | | | #2 | ATGCAGCATTGTCTTTGTCTGTCCC |
| | | | #3 | TTGTTTCTTCGGCTAAAGGTACAGT |
| | | | #4 | GTACAGTTCCTTTCAAGAGGTAACA |
| | | | #5 | GAGAAATTCGAGACCATTTTGCAAG |
| | | | #6 | GGCTCAGTTCTTGAAAAACGGTGTC |
| | | | #7 | TGGGGATGAAGGCACAGGCGTCTCC |
| | | | #8 | GTGGGGTCAGGACACAGAGTGGGAG |
| | | | #9 | GAGACTGATGCAGGCCTACCAGTCC |
| | | | #10 | TGGCTTTTTGTCTGGGGCTGGAATA |
| | | | #11 | GGCTGGAATAAAGAGGTGCCTTCAG |

It is envisioned that many other probes that have an oligonucleotide length of at least about 20 to 70 nucleotides and that have binding affinity for the biomarker genes identified here (NOX4, CDX2, MMP3, FAM69A) may be identified and used according to the present invention employing the teachings rendered here together without an undue amount of trial and error. Standard molecular biology techniques and teachings, such as those provided in Carlson, S., et al. (2011), Molecular Biology Techniques, $3^{rd}$ Edition, Academic Press, may be used to identify specific oligonucleotide probes, and then used together with or instead of those specific genetic probes identified here with equal if not improved efficacy.

EXAMPLE 10

Prognostic Probes and Development thereof for RCC and LCC

The various probes identified in Tables 2, 3, 4 and 5 were employed in the various examples provided here, and found to render robust and highly prognostic data concerning colon cancer relapse, survival probabilities and expected likelihood of favorable response to chemotherapy. In some embodiments, the particular gene probes used are provided in Table 6. These particular probes are commercially available. The above specification, examples and data provide a complete description of the manufacture and use of the composition of the invention. Since many embodiments of the invention can be made without departing from the spirit and scope of the invention, the invention resides in the claims hereinafter appended.

TABLE 6

Probes (SEQ ID NOS 7-197, respectively, in order of appearance)

| | | | | LEFT-SIDE Probes |
|---|---|---|---|---|
| 205828_at | MMP3 | NM_002422 | #1 | GAAAATCGATGCAGCCATTTCTGAT |
| | | | #2 | TTTATTTCTTTACTGGATCTTCACA |
| | | | #3 | GATCTTCACAGTTGGAGTTTGACCC |
| | | | #4 | TAATTCTTCACCTAAGTCTCTGTGA |
| | | | #5 | ATTGAAATGTTCGTTTTCTCCTGCC |
| | | | #6 | GTGACTCGAGTCACACTCAAGGGAA |
| | | | #7 | TGAGCGTGAATCTGTATCTTGCCGG |
| | | | #8 | GTATCTTGCCGGTCATTTTTATGTT |
| | | | #9 | CAAATGGGCTGCTGCTTAGCTTGCA |
| | | | #10 | TTAGCTTGCACCTTGTCACATAGAG |
| | | | #11 | GGGGAAGCACTCGTGTGCAACAGAC |
| 230748_at | SLC16A6 | AI873273 | #1 | GGTTACAGGTACACACAAGCTTGAA |
| | | | #2 | TGTAGAGCATCTTATCAGCCATAGA |
| | | | #3 | GGATGTAGCAAATCTCTGTCACTGC |
| | | | #4 | CTCTGTCACTGCTTGAGAACTTTGA |
| | | | #5 | GAGCTTGTGGCAGTTTTGCAGACTT |
| | | | #6 | GACTTACATGACTTCAGCACTTTAC |
| | | | #7 | AGCACTTTACGACATATTTTTTACT |
| | | | #8 | ACTGATTTCTGAGGGATCTGCTCCA |
| | | | #9 | ATCTGCTCCATGTCTATTCTGTTAT |
| | | | #10 | GTATGCCAATTTCAGTATGTCAATA |
| | | | #11 | GACATTCTGGTACTTCTAGATTTGC |

TABLE 6-continued

Probes (SEQ ID NOS 7-197, respectively, in order of appearance)

| | | | | |
|---|---|---|---|---|
| 205990_s_at | WNT5A | NM_003392 | #1 | ATCACCTCAGCCAACTGTGGCTCTT |
| | | | #2 | CAACTGTGGCTCTTAATTTATTGCA |
| | | | #3 | GCATAATGATATTCACATCCCCTCA |
| | | | #4 | ACATCCCCTCAGTTGCAGTGAATTG |
| | | | #5 | GATTGTTCCTTTTTAGTGACTCATG |
| | | | #6 | GTTGAGTTTAACAATCCTAGCTTTT |
| | | | #7 | AAATATTCTACATGTCATTCAGATA |
| | | | #8 | ATTATGTATATCTTCTAGCCTTTAT |
| | | | #9 | ATCTTCTAGCCTTTATTCTGTACTT |
| | | | #10 | ACATATTTCTGTCTTGCGTGATTTG |
| | | | #11 | GCGTGATTTGTATATTTCACTGGTT |
| 202435_s_at | CYP1B1 | AU154504 | #1 | GAGTCAAAGACTTAAAGGGCCCAAT |
| | | | #2 | ACATACTGCATCTTGGTTATTTCTG |
| | | | #3 | TCTGAAGGTAGCATTCTTTGGAGTT |
| | | | #4 | CCCAAACACTTACACCAAACTACTG |
| | | | #5 | TGGTAACCAGGCCATTTTTGGTGGG |
| | | | #6 | GGGAATCCAAGATTGGTCTCCCATA |
| | | | #7 | GATTGGTCTCCCATATGCAGAAATA |
| | | | #8 | TAGACTCTAGTATTTATGGGTGGAT |
| | | | #9 | ATCCTTTTGCCTTCTGGTATACTTC |
| | | | #10 | ACTCCAAGGTGATGTTGTACCTCTT |
| | | | #11 | GTACCTCTTTTGCTTGCCAAAGTAC |
| 219773_at | NOX4 | NM_016931 | #1 | TATAGGACGTCCTCGGTGGAAACTT |
| | | | #2 | GTGTTTTCTGTTGTGGACCCAATTC |
| | | | #3 | CCCAATTCACTATCCAAGACTCTTC |
| | | | #4 | AACTTTTGCCATGAAGCAGGACTCT |
| | | | #5 | GGAATCAATCAGCTGTGTTATGCCA |
| | | | #6 | GTGGCAACATGACCGTCACATTACA |
| | | | #7 | GATGCACACTGTTGATTTTCATGGT |
| | | | #8 | ATGGTGGATTCAAGAACTCCCTAGT |
| | | | #9 | AGCTGAACTTGCTCAATCTAAGGCT |
| | | | #10 | TAAGGCTGATTGTCGTGTTCCTCTT |
| | | | #11 | TGTCGTGTTCCTCTTTAAATTGTTT |
| 236028_at | IBSP | BE466675 | #1 | GAAGTTCAACTCAGGAAGGTGCAAT |
| | | | #2 | GTACTACCGTTCCAGATTTCTGTA |
| | | | #3 | CAAAGTAATAGGCTTCTTGTCCCTT |
| | | | #4 | CCCTTTTTTTTCTGGCATGTTATGG |
| | | | #5 | TTATCAAGCAGTACACCAACTCATA |
| | | | #6 | ATAGTAGTTTTTAACATGCCTGTAG |
| | | | #7 | ATGCCTGTAGTATTGCTAACTGCAA |
| | | | #8 | AGTTTCTTAATCGCACTACCTATGC |
| | | | #9 | CGCACTACCTATGCAACACTGTGTA |
| | | | #10 | ACACTGTGTATTAGGTTTATCATCC |
| | | | #11 | GTGACCTGTATGTATATTCTAATCT |
| U85658 | TFAP2C | U85658 | #3 | AGCAATTTGTTGCTGCTTGTCACCC |
| | | | #4 | CAAGTCCCCGTGGAGGTTCTGTATT |
| | | | #5 | GAAACAGTGCGTTGAGTGTACAGAT |
| | | | #6 | GGGTCTGTAAATACTGGTGCACTTC |
| | | | #7 | GTGCACTTCTTACGACTTTTTTGAG |
| | | | #8 | CAATAACTTTGTCTCGTTCCTGTTG |
| | | | #9 | GTTCCTGTTGGGCTGAACCCTAAGG |
| | | | #10 | TTGGAATTGAACTCTCTGCCTGTAA |
| | | | #11 | AATGTTCCCCAAATAATTGTTGTGT |
| 206091_at | MATN3 | NM_002381 | #1 | TTTTGCTTATTTTGTTGGAGTATTA |
| | | | #2 | AAGTGAACATTACATTGCCATTTTT |
| | | | #3 | ATTTTGCTTCAGGATCCAAGTGACA |
| | | | #4 | GTCTTTTTAATGTTAGTGATCCACC |
| | | | #5 | GATTACAGGCTTGAAAGTCTAACTT |
| | | | #6 | TTGATACATATAATTCTTTTGGCTT |
| | | | #7 | TGCACTGCTCAATTCTGTTTTTCGT |
| | | | #8 | TCTGTTTTTCGTTTGCATTGTCTTT |
| | | | #9 | TTACCTTTACATATTATCATGTCTA |
| | | | #10 | TCATGTCTATTTTTGATGACTCATC |
| | | | #11 | GATGACTCATCAATTTTGTCTATTA |
| 204672_s_at | ANKRD6 | NM_014942 | #1 | ACAGAACAGGCTCAGTCAGCATCCT |
| | | | #2 | AGCATCCTCACCCAGAGATGGCAAC |
| | | | #3 | GGCAACATCTATTAAGACCAATGCA |
| | | | #4 | GACCAATGCAATACCTTTTCATCTT |

TABLE 6-continued

Probes (SEQ ID NOS 7-197, respectively, in order of appearance)

|  |  |  |  |  |
|---|---|---|---|---|
|  |  |  | #5 | ATACCTTTTCATCTTCAGCAAATGT |
|  |  |  | #6 | TGTTTTTGATCCTTGGCATTGTCAA |
|  |  |  | #7 | GGTCCAGTGTATATTTTTCCTTATT |
|  |  |  | #8 | TTTTCCCTTTTAGCTATCTGCTAAA |
|  |  |  | #9 | AAATGCCACAACTGTACTTTTCCAA |
|  |  |  | #10 | TGACAACTTATAGCCTGTCATGCAG |
|  |  |  | #11 | GCAGGTCATGTTTCAAATCAAGGCT |

RIGHT-SIDE Probes

| 216044_x_at | FAM69A | AK027146 | #1 | TATACACCCATTTTTAACCTCATTT |
|---|---|---|---|---|
|  |  |  | #2 | CAAAGGGCCCATCTTAGTATCACGC |
|  |  |  | #3 | TAGTATCACGCAGCTGACTGAGCCC |
|  |  |  | #4 | GACTGAGCCCTTCAAAACTGACATC |
|  |  |  | #5 | AAAACTGACATCTTAAGGCCCAATC |
|  |  |  | #6 | AGGCCCAATCAAGATCCACATATCC |
|  |  |  | #7 | GTATATCCTGTGGGCCAAAGGGCTA |
|  |  |  | #8 | TATCTAATGTTTTTTTCCCCATGTA |
|  |  |  | #9 | TTAGTATTTGCTCCTCTTTCATATT |
|  |  |  | #10 | TTCACACGTATACTCAGATTTGGCA |
|  |  |  | #11 | TGGCATGTACCTTTCAACATCTCCA |
| 206387_at | CDX2 | U51096 | #1 | GACAAGTGGGATTTGGGGCCTCAAG |
|  |  |  | #2 | GGGCCTCAAGAAATATACTCTCCCA |
|  |  |  | #4 | GGCTTCATTCCGGACTGGCAGAAGC |
|  |  |  | #8 | TGACCAAAGACTGCAGAACCCCCAG |
|  |  |  | #9 | GAGGGGTGGTTATTGGACTCCAGG |
|  |  |  | #11 | TAGAGAGCCTGTCACCAGAGCTTCT |
| 225582_at | ITPRIP | AA425726 | #1 | CTCGGCTGTGATCAGGGCAACCAAA |
|  |  |  | #2 | TTAGACTGAACATGTGCTTGGGCCT |
|  |  |  | #3 | CTCTCCCTAGACGCAGTTGCGGGGC |
|  |  |  | #4 | TGCGGGGCACTCCAGGGAATGAACC |
|  |  |  | #5 | ATGAACCAGCTCAAGTGTGTCCCTA |
|  |  |  | #6 | CCTCCTCATTCCATCAGATGCATTT |
|  |  |  | #7 | TGCTTTGAAGAGACCCCAGTAACCA |
|  |  |  | #8 | AAGCCAAAACCATGCCTGGATCTCC |
|  |  |  | #9 | ATCTTCTGGCTTCTTGTGTGTACAG |
|  |  |  | #10 | GAATCTTTTCTGCACCAAAGCTGCT |
|  |  |  | #11 | GGTGTTTCATGCTGCCTTATTTATA |
| 201474_s_at | ITGA3 | NM_002204 | #1 | GCCACAGACTGAACTCGCAGGGAGT |
|  |  |  | #2 | GCAAACGGCAACGTAGCCTGGGCTC |
|  |  |  | #3 | ATGGCGGGATCCTCCACAGAGAGGA |
|  |  |  | #4 | AGCCTCCAGAAGGCCCCAGAGAGAC |
|  |  |  | #5 | GACCCTGCAAGACCACGGAGGGAGC |
|  |  |  | #6 | GGAGGGAGCCGACACTTGAATGTAG |
|  |  |  | #7 | CCAGCTGAACCATGCGTCAGGGGCC |
|  |  |  | #8 | GTCAGGGGCCTAGAGGTGGAGTTCT |
|  |  |  | #9 | GTGGAGTTCTTAGCTATCCTTGGCT |
|  |  |  | #10 | GTGTCCTAAGGCCCATTTGAGAAGC |
|  |  |  | #11 | AGGCTAGTTCCAAAAACCTCTCCTG |
| 225667_s_at | FAM84A | AI601101 | #1 | ATAGCATCTATGTCTCTTTCAAGGG |
|  |  |  | #2 | GACAGCAAGTATTATGGCCAAAGCC |
|  |  |  | #3 | AAAGCCAGTTTCTTGGCATTTCAAA |
|  |  |  | #4 | TGGTTTTCATCCTGGATTCATCCCC |
|  |  |  | #5 | GGATTCATCCCCTGATCTTAAATCA |
|  |  |  | #6 | TAATAACTAACTTACCTTTGCATGT |
|  |  |  | #7 | AACTTACTCCTCTTTCAAGTAACAG |
|  |  |  | #8 | TATTGTATCTACACACTCCACATTC |
|  |  |  | #9 | CATTCTTTACTGTGTCCTACTACTG |
|  |  |  | #10 | TGTGTCCTACTACTGTATCTTGGCT |
|  |  |  | #11 | TCTTGGCTCCCTGCTGTATTAAACA |
| 227123_at | RAB3B | AU156710 | #1 | GAGGCTTCCCTCAGATCAAGGAGCC |
|  |  |  | #2 | GCAGATGATCTATCTCTGTGGCCAC |
|  |  |  | #3 | GAGATGTCACCTTATGCAATTTGCA |
|  |  |  | #4 | TGCATATCATATTCAATTCCCCCAA |
|  |  |  | #5 | CCCAACTGCTCTTTCTAATTTATTC |
|  |  |  | #6 | ATTCAACTGGGGACCAGGCTGGTCT |
|  |  |  | #7 | TGGTCTCATGCCAACCTAGGAGATG |
|  |  |  | #8 | TGCAGTTGCCTCTCGATAGGCCTGA |
|  |  |  | #9 | GAGGAACAATAGCTCTCACGTCTCT |
|  |  |  | #10 | TCTCCTCATCAGATTCTAACTAAGC |
|  |  |  | #11 | ATCTATGGTGTTTCCTTGTTCTGTG |

TABLE 6-continued

| Probes (SEQ ID NOS 7-197, respectively, in order of appearance) | | | | |
|---|---|---|---|---|
| 218284_at | SMAD3 | NM_015400 | #1 | GGTGTAGTGGCTTTTTGGCTCAGCA |
| | | | #2 | GGCTCAGCATCCAGAAACACCAAAC |
| | | | #3 | GGCTGGCTAAACAAGTGGCCGCGTG |
| | | | #4 | CAGCTCTGAGTCAAATCTGGGCCCT |
| | | | #5 | CCCACTCCCTTGCTAGGGGTGAAAG |
| | | | #6 | GAGCCATCTATCCAAGAAGCCTTCA |
| | | | #7 | CTGTTCTGGACTCTGATGTGTGTGG |
| | | | #8 | GCCAGCCTGACCTTTTAATAACTTT |
| | | | #9 | GCACCTGTTTAAGCATTGTACCCCT |
| | | | #10 | GTTAAAGATTTGTGTCCTCTCATTC |
| | | | #11 | TCCTCTTGTAAGTGCCCTTCTAATA |
| 205559_s_at | PCSK5 | NM_006200 | #1 | GCAACGGAAGAGTCCTGGGCGGAAG |
| | | | #2 | GAGTCCTGGGCGGAAGGAGGCTTCT |
| | | | #3 | GAAGGAGGCTTCTGTATGCTTGTGA |
| | | | #4 | GAGGCTTCTGTATGCTTGTGAAAAA |
| | | | #5 | GAAAAAGAACAATCTGTGCCAACGG |
| | | | #6 | AATCTGTGCCAACGGAAGGTTCTTC |
| | | | #7 | TGTGCCAACGGAAGGTTCTTCAACA |
| | | | #8 | ATTTCAAGGCTGAGCAGCCATCTTA |
| | | | #9 | GGCTGAGCAGCCATCTTAGATTTCT |
| | | | #10 | GAGCAGCCATCTTAGATTTCTTTGT |
| | | | #11 | ATTTCTTTGTTCCTGTAGACTTATA |
| 219909_at | MMP28 | NM_024302 | #1 | CCTTTGTTCCTTGAAGAATGCAGCA |
| | | | #2 | ATGCAGCATTGTCTTTGTCTGTCCC |
| | | | #3 | TTGTTTCTTCGGCTAAAGGTACAGT |
| | | | #4 | GTACAGTTCCTTTCAAGAGGTAACA |
| | | | #5 | GAGAAATTCGAGACCATTTTGCAAG |
| | | | #6 | GGCTCAGTTCTTGAAAAACGGTGTC |
| | | | #7 | TGGGGATGAAGGCACAGGCGTCTCC |
| | | | #8 | GTGGGGTCAGGACACAGAGTGGGAG |
| | | | #9 | GAGACTGATGCAGGCCTACCAGTCC |
| | | | #10 | TGGCTTTTTGTCTGGGGCTGGAATA |
| | | | #11 | GGCTGGAATAAAGAGGTGCCTTCAG |

What is claimed is:

1. A panel of probes for indicating a 5-year left-side colon cancer (LCC) relapse probability of LCC in a post-surgery human LCC patient, said panel of probes consisting of detectably labeled single-stranded polynucleotides complementary to mRNA or cDNA of two or more genes selected from the group consisting of NOX4, MMP3, SLC16A6, WNT5A, CYP1B1, IBSP, TFAP2C, MATN3 and ANKRD6.

2. The panel of probes of claim 1, wherein the detectably labeled single-stranded polynucleotides are immobilized to a solid surface.

3. The panel of probes of claim 1, wherein the detectable label is a fluorescent label or a radiolabel.

4. The panel of probes of claim 2, wherein the solid surface is nylon, plastic, silicon, or ceramic.

5. The panel of probes of claim 2 wherein the solid surface is a silicon wafer.

6. The panel of probes of claim 2 wherein the solid surface is a glass.

7. The panel of probes of claim 6 wherein the solid surface is a glass slide or a glass chip.

8. The panel of probes of claim 2 wherein the probes are fixed to the solid surface by a covalent bond.

9. The panel of probes of claim 1 wherein the probes are fixed to a solid surface in a kit form.

10. The panel of probes of claim 9, wherein the detectable label of the probes is a fluorescent label or a radiolabel.

11. The panel of probes of claim 9, wherein the solid surface is nylon, plastic, silicon, or ceramic.

12. The panel of probes of claim 9 wherein the solid surface is a silicon wafer.

13. The panel of probes of claim 9 wherein the solid surface is a glass.

14. The panel of probes of claim 9 wherein the solid surface is a glass slide or a glass chip.

15. The panel of probes of claim 9 wherein the probes are fixed to the solid surface by a covalent bond.

16. A panel of probes for indicating a 5-year LCC relapse probability of LCC in a post-surgery human LCC patient, said panel of probes consisting of detectably labeled single-stranded polynucleotides complementary to mRNA or cDNA of NOX4 and MMP3.

17. The panel of probes of claim 16, wherein the detectably labeled single-stranded polynucleotides are immobilized to a solid surface.

18. The panel of probes of claim 16, wherein the detectable label is a fluorescent label or a radiolabel.

19. The panel of probes of claim 17, wherein the solid surface is nylon, plastic, silicon, or ceramic.

20. The panel of probes of claim 17 wherein the solid surface is a silicon wafer.

21. The panel of probes of claim 17 wherein the solid surface is a glass.

22. The panel of probes of claim 21 wherein the solid surface is a glass slide or a glass chip.

23. The panel of probes of claim 17 wherein the probes are fixed to the solid surface by a covalent bond.

24. A panel of probes for indicating a 5-year left-side colon cancer (LCC) relapse probability of LCC in a post-surgery human LCC patient, said panel of probes consisting of detectably labeled single-stranded polynucleotides complementary to mRNA or cDNA of at least five genes selected from the group consisting of NOX4, MMP3, SLC16A6, WNT5A, CYP1B1, IBSP, TFAP2C, MATN3 and ANKRD6.

25. The panel of probes of claim 24, wherein the detectably labeled single-stranded polynucleotides are immobilized to a solid surface.

26. The panel of probes of claim 24, wherein the detectable label is a fluorescent label or a radiolabel.

27. The panel of probes of claim 25, wherein the solid surface is nylon, plastic, silicon, or ceramic.

28. The panel of probes of claim 25 wherein the solid surface is a silicon wafer.

29. The panel of probes of claim 25 wherein the solid surface is a glass.

30. The panel of probes of claim 25 wherein the solid surface is a glass slide or a glass chip.

31. The panel of probes of claim 25 wherein the probes are fixed to the solid surface by a covalent bond.

* * * * *

SEQUENCE LISTING

<160> NUMBER OF SEQ ID NOS: 197

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ccaggagauu guuggauaat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gaguuuccau agggaacuat t                                              21

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccatgaagc aggactctaa aga                                            23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttggcataac acagctgatt gat                                            23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgtcagttg ctgcattcct aa                                             22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcactcaata gtgctgtggt tt                                             22

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gaaaatcgat gcagccattt ctgat                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tttatttctt tactggatct tcaca                                          25
```

```
<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gatcttcaca gttggagttt gaccc                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
taattcttca cctaagtctc tgtga                                          25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
attgaaatgt tcgttttctc ctgcc                                          25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gtgactcgag tcacactcaa gggaa                                          25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tgagcgtgaa tctgtatctt gccgg                                          25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gtatcttgcc ggtcattttt atgtt                                          25

<210> SEQ ID NO 15
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
caaatgggct gctgcttagc ttgca                                           25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ttagcttgca ccttgtcaca tagag                                           25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ggggaagcac tcgtgtgcaa cagac                                           25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ggttacaggt acacacaagc ttgaa                                           25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tgtagagcat cttatcagcc ataga                                           25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ggatgtagca aatctctgtc actgc                                           25

<210> SEQ ID NO 21
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ctctgtcact gcttgagaac tttga                                            25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gagcttgtgg cagttttgca gactt                                            25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gacttacatg acttcagcac tttac                                            25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
agcactttac gacatatttt ttact                                            25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
actgatttct gagggatctg ctcca                                            25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
atctgctcca tgtctattct gttat                                            25

<210> SEQ ID NO 27
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 27
gtatgccaat tcagtatgt caata                                           25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gacattctgg tacttctaga tttgc                                          25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
atcacctcag ccaactgtgg ctctt                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
caactgtggc tcttaattta ttgca                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
gcataatgat attcacatcc cctca                                          25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
acatcccctc agttgcagtg aattg                                          25

<210> SEQ ID NO 33
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 33
gattgttcct ttttagtgac tcatg                                          25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
gttgagttta acaatcctag ctttt                                          25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
aaatattcta catgtcattc agata                                          25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
attatgtata tcttctagcc tttat                                          25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
atcttctagc ctttattctg tactt                                          25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
acatatttct gtcttgcgtg atttg                                          25

<210> SEQ ID NO 39
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 39
gcgtgatttg tatatttcac tggtt                                              25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
gagtcaaaga cttaaagggc ccaat                                              25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
acatactgca tcttggttat ttctg                                              25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
tctgaaggta gcattctttg gagtt                                              25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
cccaaacact tacaccaaac tactg                                              25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tggtaaccag gccatttttg gtggg                                              25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 45
gggaatccaa gattggtctc ccata                                          25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
gattggtctc ccatatgcag aaata                                          25

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
tagactctag tatttatggg tggat                                          25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
atccttttgc cttctggtat acttc                                          25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
actccaaggt gatgttgtac ctctt                                          25

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
gtacctcttt tgcttgccaa agtac                                          25

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tataggacgt cctcggtgga aactt                                              25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
gtgttttctg ttgtggaccc aattc                                              25

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
cccaattcac tatccaagac tcttc                                              25

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54 aactttgcc atgaagcagg actct                                               25

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
ggaatcaatc agctgtgtta tgcca                                              25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
gtggcaacat gaccgtcaca ttaca                                              25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 57
gatgcacact gttgattttc atggt                                           25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
atggtggatt caagaactcc ctagt                                           25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
agctgaactt gctcaatcta aggct                                           25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
taaggctgat tgtcgtgttc ctctt                                           25

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
tgtcgtgttc ctctttaaat tgttt                                           25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
gaagttcaac tcaggaaggt gcaat                                           25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
```

```
gtactaccgt tccagatttt ctgta                                              25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
caaagtaata ggcttcttgt ccctt                                              25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
cccttttttt tctggcatgt tatgg                                              25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
ttatcaagca gtacaccaac tcata                                              25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
atagtagttt ttaacatgcc tgtag                                              25

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
atgcctgtag tattgctaac tgcaa                                              25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
```

```
agtttcttaa tcgcactacc tatgc                                           25

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
cgcactacct atgcaacact gtgta                                           25

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
acactgtgta ttaggtttat catcc                                           25

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
gtgacctgta tgtatattct aatct                                           25

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
agcaatttgt tgctgcttgt caccc                                           25

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
caagtccccg tggaggttct gtatt                                           25

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
gaaacagtgc gttgagtgta cagat                                           25
```

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
gggtctgtaa atactggtgc acttc                                              25

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
gtgcacttct tacgactttt ttgag                                              25

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
caataacttt gtctcgttcc tgttg                                              25

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
gttcctgttg ggctgaaccc taagg                                              25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
ttggaattga actctctgcc tgtaa                                              25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
aatgttcccc aaataattgt tgtgt                                              25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
ttttgcttat tttgttggag tatta                                              25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
aagtgaacat tacattgcca ttttt                                              25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
attttgcttc aggatccaag tgaca                                              25

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85 gtcttttta tgttagtgat ccacc                                               25

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
gattacaggc ttgaaagtct aactt                                              25

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
ttgatacata taattctttt ggctt                                              25

-continued

```
<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
tgcactgctc aattctgttt ttcgt                                              25

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89 tctgttttc gtttgcattg tcttt                                               25

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ttacctttac atattatcat gtcta                                              25

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
tcatgtctat ttttgatgac tcatc                                              25

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
gatgactcat caattttgtc tatta                                              25

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
acagaacagg ctcagtcagc atcct                                              25

<210> SEQ ID NO 94
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
agcatcctca cccagagatg gcaac                                              25

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ggcaacatct attaagacca atgca                                              25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
gaccaatgca ataccttttc atctt                                              25

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
ataccttttc atcttcagca aatgt                                              25

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98 tgttttgat ccttggcatt gtcaa                                               25

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ggtccagtgt atattttcc ttatt                                               25

<210> SEQ ID NO 100
<211> LENGTH: 25
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100 ttttccctttt tagctatctg ctaaa                                     25

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
aaatgccaca actgtacttt tccaa                                      25

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tgacaactta tagcctgtca tgcag                                      25

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
gcaggtcatg tttcaaatca aggct                                      25

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tatacaccca tttttaacct cattt                                      25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
caaagggccc atcttagtat cacgc                                      25

<210> SEQ ID NO 106
<211> LENGTH: 25
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 106
tagtatcacg cagctgactg agccc                                        25

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
gactgagccc ttcaaaactg acatc                                        25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
aaaactgaca tcttaaggcc caatc                                        25

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
aggcccaatc aagatccaca tatcc                                        25

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
gtatatcctg tgggccaaag ggcta                                        25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
tatctaatgt tttttccccc atgta                                        25

<210> SEQ ID NO 112
<211> LENGTH: 25
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 112
ttagtatttg ctcctctttc atatt                                               25

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
ttcacacgta tactcagatt tggca                                               25

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
tggcatgtac ctttcaacat ctcca                                               25

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
gacaagtggg atttggggcc tcaag                                               25

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
gggcctcaag aaatatactc tccca                                               25

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ggcttcattc cggactggca gaagc                                               25

<210> SEQ ID NO 118
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 118
tgaccaaaga ctgcagaacc cccag                                              25

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119 gaggggtgg ttattggact ccagg                                               25

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
tagagagcct gtcaccagag cttct                                              25

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
ctcggctgtg atcagggcaa ccaaa                                              25

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
ttagactgaa catgtgcttg ggcct                                              25

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
ctctccctag acgcagttgc ggggc                                              25

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 124
tgcggggcac tccagggaat gaacc                                              25

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
atgaaccagc tcaagtgtgt cccta                                              25

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
cctcctcatt ccatcagatg cattt                                              25

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
tgctttgaag agacccagt aacca                                               25

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
aagccaaaac catgcctgga tctcc                                              25

<210> SEQ ID NO 129
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
atcttctggc ttcttgtgtg tacag                                              25

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
gaatcttttc tgcaccaaag ctgct                                        25

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
ggtgtttcat gctgccttat ttata                                        25

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
gccacagact gaactcgcag ggagt                                        25

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
gcaaacggca acgtagcctg ggctc                                        25

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
atggcgggat cctccacaga gagga                                        25

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
agcctccaga aggccccaga gagac                                        25

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
gaccctgcaa gaccacggag ggagc                                           25

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
ggagggagcc gacacttgaa tgtag                                           25

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
ccagctgaac catgcgtcag gggcc                                           25

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
gtcaggggcc tagaggtgga gttct                                           25

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
gtggagttct tagctatcct tggct                                           25

<210> SEQ ID NO 141
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
gtgtcctaag gcccatttga gaagc                                           25

<210> SEQ ID NO 142
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
aggctagttc caaaaacctc tcctg                                       25

<210> SEQ ID NO 143
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
atagcatcta tgtctctttc aaggg                                       25

<210> SEQ ID NO 144
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
gacagcaagt attatggcca aagcc                                       25

<210> SEQ ID NO 145
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
aaagccagtt tcttggcatt tcaaa                                       25

<210> SEQ ID NO 146
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
tggttttcat cctggattca tcccc                                       25

<210> SEQ ID NO 147
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
ggattcatcc cctgatctta aatca                                       25

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148

```
taataactaa cttacctttg catgt                                          25
```

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149

```
aacttactcc tctttcaagt aacag                                          25
```

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150

```
tattgtatct acacactcca cattc                                          25
```

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151

```
cattctttac tgtgtcctac tactg                                          25
```

<210> SEQ ID NO 152
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152

```
tgtgtcctac tactgtatct tggct                                          25
```

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153

```
tcttggctcc ctgctgtatt aaaca                                          25
```

<210> SEQ ID NO 154
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154

```
gaggcttccc tcagatcaag gagcc                                          25
```

```
<210> SEQ ID NO 155
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
gcagatgatc tatctctgtg gccac                                             25

<210> SEQ ID NO 156
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
gagatgtcac cttatgcaat ttgca                                             25

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
tgcatatcat attcaattcc cccaa                                             25

<210> SEQ ID NO 158
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
cccaactgct ctttctaatt tattc                                             25

<210> SEQ ID NO 159
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
attcaactgg ggaccaggct ggtct                                             25

<210> SEQ ID NO 160
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
tggtctcatg ccaacctagg agatg                                             25
```

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
tgcagttgcc tctcgatagg cctga                                           25

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
gaggaacaat agctctcacg tctct                                           25

<210> SEQ ID NO 163
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
tctcctcatc agattctaac taagc                                           25

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
atctatggtg tttccttgtt ctgtg                                           25

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
ggtgtagtgg cttttggct cagca                                            25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
ggctcagcat ccagaaacac caaac                                           25

```
<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
ggctggctaa acaagtggcc gcgtg                                           25

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
cagctctgag tcaaatctgg gccct                                           25

<210> SEQ ID NO 169
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
cccactccct tgctaggggt gaaag                                           25

<210> SEQ ID NO 170
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
gagccatcta tccaagaagc cttca                                           25

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
ctgttctgga ctctgatgtg tgtgg                                           25

<210> SEQ ID NO 172
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
gccagcctga cctttaata acttt                                            25

<210> SEQ ID NO 173
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
gcacctgttt aagcattgta ccect                                              25

<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
gttaaagatt tgtgtcctct cattc                                              25

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
tcctcttgta agtgcccttc taata                                              25

<210> SEQ ID NO 176
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
gcaacggaag agtcctgggc ggaag                                              25

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
gagtcctggg cggaaggagg cttct                                              25

<210> SEQ ID NO 178
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
gaaggaggct tctgtatgct tgtga                                              25

<210> SEQ ID NO 179
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
gaggcttctg tatgcttgtg aaaaa                                        25

<210> SEQ ID NO 180
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
gaaaaagaac aatctgtgcc aacgg                                        25

<210> SEQ ID NO 181
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
aatctgtgcc aacggaaggt tcttc                                        25

<210> SEQ ID NO 182
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
tgtgccaacg gaaggttctt caaca                                        25

<210> SEQ ID NO 183
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
atttcaaggc tgagcagcca tctta                                        25

<210> SEQ ID NO 184
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
ggctgagcag ccatcttaga tttct                                        25

<210> SEQ ID NO 185
<211> LENGTH: 25
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 185
gagcagccat cttagatttc tttgt                                       25

<210> SEQ ID NO 186
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
atttctttgt tcctgtagac ttata                                       25

<210> SEQ ID NO 187
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
cctttgttcc ttgaagaatg cagca                                       25

<210> SEQ ID NO 188
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
atgcagcatt gtctttgtct gtccc                                       25

<210> SEQ ID NO 189
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
ttgtttcttc ggctaaaggt acagt                                       25

<210> SEQ ID NO 190
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
gtacagttcc tttcaagagg taaca                                       25

<210> SEQ ID NO 191
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
gagaaattcg agaccatttt gcaag                                          25

<210> SEQ ID NO 192
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
ggctcagttc ttgaaaaacg gtgtc                                          25

<210> SEQ ID NO 193
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
tggggatgaa ggcacaggcg tctcc                                          25

<210> SEQ ID NO 194
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
gtggggtcag gacacagagt gggag                                          25

<210> SEQ ID NO 195
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
gagactgatg caggcctacc agtcc                                          25

<210> SEQ ID NO 196
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196 tggcttttg tctggggctg gaata                                           25

<210> SEQ ID NO 197
<211> LENGTH: 25
<212> TYPE: DNA
<213> ORGANISM: Artificial Sequence
<220> FEATURE:

-continued

```
<223> OTHER INFORMATION: Description of Artificial Sequence: Synthetic
      probe

<400> SEQUENCE: 197
ggctggaata aagaggtgcc ttcag                                           25
```